(12) United States Patent
Tissier et al.

(10) Patent No.: US 9,115,366 B2
(45) Date of Patent: *Aug. 25, 2015

(54) SYSTEM FOR PRODUCING TERPENOIDS IN PLANTS

(75) Inventors: Alain Tissier, Pertuis (FR); Christophe Sallaud, Montpellier (FR); Denis Rontein, Greoux les Bains (FR)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 900 days.

This patent is subject to a terminal disclaimer.

(21) Appl. No.: 11/814,943

(22) PCT Filed: Jan. 27, 2006

(86) PCT No.: PCT/FR2006/000188
§ 371 (c)(1),
(2), (4) Date: Jul. 27, 2007

(87) PCT Pub. No.: WO2006/079727
PCT Pub. Date: Aug. 3, 2006

(65) Prior Publication Data
US 2008/0281135 A1    Nov. 13, 2008

(30) Foreign Application Priority Data
Jan. 27, 2005 (FR) ..................... 05 00855

(51) Int. Cl.
| | | |
|---|---|---|
| *C12N 15/113* | (2010.01) | |
| *C12N 5/14* | (2006.01) | |
| *A01H 1/00* | (2006.01) | |
| *C12N 15/82* | (2006.01) | |
| *C12N 9/88* | (2006.01) | |
| *C12P 5/00* | (2006.01) | |
| *C12P 15/00* | (2006.01) | |

(52) U.S. Cl.
CPC .............. *C12N 15/8243* (2013.01); *C12N 9/88* (2013.01); *C12N 15/8223* (2013.01); *C12P 5/007* (2013.01); *C12P 15/00* (2013.01); *C12N 15/1137* (2013.01); *C12N 15/8205* (2013.01)

(58) Field of Classification Search
USPC ......................................................... 800/278
See application file for complete search history.

(56) References Cited

U.S. PATENT DOCUMENTS

| | | | |
|---|---|---|---|
| 6,730,826 B2 | 5/2004 | Wagner et al. | |
| 2004/0234968 A1 | 11/2004 | Croteau et al. | |
| 2006/0150283 A1* | 7/2006 | Alexandrov et al. | 800/288 |
| 2009/0300791 A1 | 12/2009 | Tissier et al. | |

FOREIGN PATENT DOCUMENTS

| | | | |
|---|---|---|---|
| WO | WO 93/07266 A1 | 4/1993 | |
| WO | WO 99/19460 A1 | 4/1999 | |
| WO | WO 99/38957 | * 8/1999 | ............ C12N 15/82 |
| WO | WO 99/38957 A1 | 8/1999 | |
| WO | WO 00/17327 A3 | 3/2000 | |
| WO | WO 01/20008 A2 | 3/2001 | |
| WO | WO 2004/111183 A2 | 12/2004 | |
| WO | WO 2006/040479 | 4/2006 | |

OTHER PUBLICATIONS

Aharoni, A et al. The Plant Cell (Dec. 2003), vol. 15; pp. 2866-2884.*
Besumbes, O. et al. Biotechnology and Bioengineering; Oct. 20, 2004; vol. 88, No. 2; pp. 168-175.*
Wang, E. et al. Nature Biotechnology, Apr. 2001; vol. 19, pp. 371-374.*
Wang, E. et al. Journal of Experimental Botany, Sep. 2002, vol. 53, No. 376; pp. 1891-1897.*
Walker K. et al. Phytochemistry (2001) vol. 58; pp. 1-7.*
Gutiérrez-Alcalá et al., A versatile promoter for the expression of proteins in glandular and non-glandular trichomes from a variety of plants, 56 J of Exp Botany No. 419, 2487-2494 (2005).*
Besumbes et al. (Metabolic Engineering of Isoprenoid Biosynthesis in *Arabidopsis* for the Production of Taxadiene, the First Committed Precursor of Taxol, 88 Biotechnology and Bioengineering No. 2, 165-175 (2004)).*
Wang et al. (Isolation and characterization of the CYP71D16 trichome-specific promoter from *Nicotiana tabacum* L., 53 J of Exp Botany No. 37, 1891-1897 at 1895-1897 (2002) (hereinafter Wang et al.2002)).*
Wang et al. (Suppression of a P450 hydroxylase gene in plant trichome glands enhances natural-product-based aphid resistance, 19 Nature Biotechnology, 371-374 (2001) (hereinafter Wang et al.2001).*
Walker et al. (Taxol biosynthetic genes, 58 Phytochemistry, 1-7 (2001)).*
Stegemann et al. (Experimental Reconstruction of Functional gene Transfer from the Tobacco Plastid Genome to the Nucleus, 18 Plant Cell, 2869-2878 (2006)).*
Lange, B. M. et al. "Genetic engineering of essential oil production in mint" *Current Opinion in Plant Biology*, 1999, pp. 139-144, vol. 2, XP-009101099.
Wang, E. et al. "Isolation and characterization of the *CYP71D16* trichome-specific promoter from *Nicotiana tabacum* L." *Journal of Experimental Botany*, Sep. 2002, pp. 1891-1897, vol. 53, No. 376, XP-002318244.

(Continued)

*Primary Examiner* — Russell Kallis
*Assistant Examiner* — Rebecca Stephens
(74) *Attorney, Agent, or Firm* — Saliwanchik, Lloyd & Eisenschenk

(57) ABSTRACT

The invention concerns a method for producing terpenes of interest in plants having glandular trichomes, as well as plants useful for producing said terpenes of interest. Said plants comprise a sequence encoding a heterologous terpene synthase under the control of a promoter enabling it to be specifically expressed in the trichomes. Moreover, the pathway for producing endogenous diterpenes is preferably blocked in the trichomes of the plants, to increase the flow in the heterologous pathway. The secretion of heterologous terpenes is spontaneous resulting in easy collection. The present invention also concerns plants exhibiting a blocked production of a compound having antibiotic properties at the surface of leaves exhibiting enhanced efficiency of transformation by a bacterium.

19 Claims, 10 Drawing Sheets
(1 of 10 Drawing Sheet(s) Filed in Color)

(56) References Cited

OTHER PUBLICATIONS

Aharoni, A. et al. "Terpenoid Metabolism in Wild-Type and Transgenic *Arabidopsis* Plants" *The Plant Cell*, Dec. 2003, pp. 2866-2884, vol. 15.

Besumbes, O. et al. "Metabolic Engineering of Isoprenoid Biosynthesis in *Arabidopsis* for the Production of Taxadiene, the First Committed Precursor of Taxol" *Biotechnology and Bioengineering*, Oct. 20, 2004, pp. 168-175, vol. 88, No. 2.

Hermann, S. R. et al. "Promoters Derived from Banana Bunchy Top Virus-Associated Components S1 and S2 Drive Transgene Expression in Both Tobacco and Banana" *Plant Cell Rep*, 2001, pp. 642-646, vol. 20.

Iijima, Y. et al. "The Biochemical and Molecular Basis for the Divergent Patterns in the Biosynthesis of Terpenes and Phenylpropenes in the Peltate Glands of Three Cultivars of Basil" *Plant Physiology*, Nov. 2004, pp. 3724-3736, vol. 136.

Liu, H.-C. et al. "Cloning and Promoter Analysis of the Cotton Lipid Transfer Protein Gene *Ltp3*" *Biochimica et Biophysica Acta*, 2000, pp. 106-111, vol. 1487.

Mahmoud, S. S. et al. "Metabolic Engineering of Essential Oil Yield and Composition in Mint by Altering Expression of Deoxyxylulose Phosphate Reductoisomerase and Menthofuran Synthase" *PNAS*, Jul. 17, 2001, pp. 8915-8920, vol. 98, No. 15.

Wang, E. et al. "Elucidation of the Functions of Genes Central to Diterpene Metabolism in Tobacco Trichomes Using Post-transcriptional Gene Silencing" *Planta*, 2003, pp. 686-691, vol. 216.

Hohn, T. et al. "Expression of a Fungal Sesquiterpene Cyclase Gene in Transgenic Tobacco" *Plant Physiol.*, 1991, pp. 460-462, vol. 97.

\* cited by examiner

SYSTEM FOR PRODUCING TERPENOIDS IN PLANTS

CROSS-REFERENCE TO RELATED APPLICATION

This application is the U.S. national stage application of International Patent Application No. PCT/FR2006/000188, filed Jan. 27, 2006, the disclosure of which is hereby incorporated by reference in its entirety, including all figures, tables and amino acid or nucleic acid sequences.

FIELD OF THE INVENTION

The invention relates to a method for producing compounds of interest in plants and to genetically modified plants prepared for use in said method. The invention also relates to genetically modified plants enabling an enhanced efficiency of transformation.

INTRODUCTION

Trichomes are organs located at the surfaces of the aerial parts of higher plants (reviewed in Wagner et al., 2004). They take various forms and are classified into two main categories. The first includes hairs, or non-secreting trichomes, unicellular or multicellular. They do not secrete substances to the exterior, or at least not in appreciable amounts. The second group comprises all trichomes described as secreting or glandular, which have an increased capacity to synthesize and secrete various substances to the exterior. Several types of secreting trichomes are found in this category. In particular these include the peltate trichomes, from the Lamiaceae family for example (mint, basil, lavender, thyme, etc.) and the glandular trichomes found among others in the Solanaceae (tomato, tobacco, potato, pepper, eggplant, etc.), Asteraceae (sunflower, etc.) and Cannabaceae (eg. *Cannabis sativa*) families.

The peltate trichomes of Lamiaceae are the site of production of volatile molecules, such as monoterpenes (eg., menthol, terpineol). Their structure is characterized by an oil sac located between the apical periplasma membrane of the secretory cells and a wall, in which the volatile oils accumulate (Turner et al., 2000). It is when these sacs break, for example when the leaf is crumpled, that the essential oils are released.

Trichomes described as secreting preferably synthesize molecules which have low or no volatility at ambient temperature, such as sesquiterpenes or diterpenes (Wagner et al., 2004). The glandular trichomes of cultivated tobacco (*Nicotiana tabacum*) for example, produce a secretion over half of which is composed of dipterpenes belonging to two classes, the cembranes and the labdanes (Heemann et al., 1983). In some species of wild tobacco such as *Nicotiana sylvestris*, only the cembranoids, and more particularly cembratriene-diol (CBT-diol), are present and the quantities which accumulate at the leaf surface account for about 15% of the leaf dry matter (Severson et al., 1985).

All diterpenes originate from the same precursor substrate, geranylgeranyldiphosphate (GGPP). What accounts for the diversity of diterpenes are the terpene synthases which use GGPP to produce an olefin, cyclic or not. GGPP is also the precursor of tetraterpenes, among which are found the carotenoid pigments. The diterpenes include molecules of primary metabolism, such as the gibberellins, which are plant growth hormones, and secondary metabolites which account for most of the metabolic diversity of these molecules. This division between primary and secondary metabolites takes place through a tight regulation of the metabolic availability of GGPP. In this respect, it is relevant to note that plant species which accumulate large amounts of diterpenes are equipped with specialised organs, the secreting trichomes, dedicated to the synthesis thereof. Tobacco and in particular *Nicotiana sylvestris*, are a typical example where there is an abundant GGPP pool in the trichomes in order to ensure a high flow of cembranoid synthesis, and hence the high accumulation thereof at the surface of the aerial parts.

The steps leading to the biosynthesis of CBT-diol in tobacco have been partially elucidated and can be broken down into two different parts:

- biosynthesis of the universal precursor of all diterpenes, geranylgeranyl pyrophosphate (GGPP), via the so-called "Rohmer" pathway (Rohmer et al., 1996), takes place in the chloroplast.
- biosynthesis of CBT-diol from GGPP. Wang and Wagner (2003) have proposed the following biosynthetic pathway:

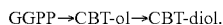

GGPP→CBT-ol→CBT-diol.

The first cyclization step would be carried out by an enzyme from a large family of enzymes known as terpene synthases (Bohlmann et al., 1998). The diterpene synthase of tobacco would use GGPP as substrate to form CBT-ol. The second step whereby CBT-diol is produced from CBT-ol is a hydroxylation catalyzed by an enzyme from the cytochrome P450 family. Professor G. Wagner's group (University of Kentucky) has used subtractive PCR to identify two *N. tabacum* candidate genes for each of these steps:

- a sequence displaying high homology with sequences coding for terpene synthases (CYC-2; Genbank No. AF401234. NID: AY495694),
- a sequence coding for a cytochrome P450-type enzyme (CYP71D16, NID: AF166332) (Wang et al., 2001, Wang & Wagner 2003).

Studies of the silencing of expression of these genes by co-suppression and RNA interference in *N. tabacum* have shown (i) a decrease in CBT-diol and CBT-ol correlated with a decrease in CYC-2 gene expression, and (ii) an increase in CBT-ol accumulation and a decrease in CBT-diol formation correlated with a decrease in CYP71D16 gene expression in the trichomes. These studies have suggested that (i) the CYC-2 gene codes for the CBT-ol cyclase responsible for CBT-ol synthesis and (ii) the CYP71D16 gene codes for a CBT-ol hydroxylase which converts CBT-ol to CBT-diol. Moreover, a genomic sequence of a gene very similar to CYC-2 mRNA has recently been deposited in the data base (CYC-1, NID: AY049090), which suggests the existence of not one but several CBT-ol cyclase genes.

Certain diterpenoids have been commercially exploited, particularly in the pharmaceutical sector. This is true in particular for diterpenoids from the taxane class, paclitaxel and docetaxel, used in the treatment of breast and ovarian cancer. Paclitaxel is a natural molecule extracted from the yew (*Taxus* sp.), while docetaxel is a semi-synthetic molecule, derived from a paclitaxel precursor, 10-deacetyl baccatin III (or 10-DAB III), also extracted from yew. Most of the paclitaxel biosynthetic genes of yew have been described (Jennewein & Croteau, 2001; Jennewein et al., 2004). These molecules are costly to produce due to the relatively low abundance of 10-DAB III and especially of paclitaxel in yew extracts, and due to the absence of a synthetic method that can be scaled up industrially, on account of the structural complexity of the molecules.

Thus there is a high demand for methods for producing terpenes of interest at a lower cost, but also for producing terpene derivatives that are not yet easily accessible to synthesis.

SUMMARY OF THE INVENTION

The present invention describes a novel method for producing terpenes of interest in plants having glandular trichomes, as well as plants useful for said production. Said novel method is based on introducing into the plant a heterologous terpene synthase enabling production of the terpene of interest. The expression of said heterologous terpene synthase is controlled by a promoter enabling an expression, preferably specific, in the glandular trichomes of the plant. To increase the yield, it is preferable to block the synthesis of endogenous diterpenes in the trichomes of the plant.

A first object of the invention relates to a method for producing a terpene of interest in a plant having glandular trichomes comprising:
a) introducing into a cell of said plant a construct containing an expression cassette comprising a polynucleotide sequence encoding a heterologous terpene synthase enabling the synthesis of said terpene of interest under the control of a promoter enabling an expression, preferably specific, in the trichomes;
b) reconstituting a plant from said cell and selecting transgenic plants expressing said terpene synthase; and
c) recovering the terpene of interest contained in the trichomes of said transgenic plants.

Preferably, the expression of the terpene synthase is under the control of a trichome-specific promoter.

Preferably, the recovery of the terpene of interest in the trichomes of said transgenic plants is carried out by collecting the terpene of interest contained in the trichome exudate.

In a particular preferred embodiment, said expression cassette comprises at least one enhancer sequence operably linked to the promoter. In a particular embodiment, the enhancer sequence comprises the sequence SEQ ID No 9.

Preferably, the method additionally comprises blocking the pathway of endogenous diterpene production in the trichomes. More particularly, the endogenous diterpene production pathway can be blocked by blocking the expression of endogenous diterpene synthase(s). Preferably, blocking the endogenous diterpene production pathway in the trichomes is carried out by crossing the transgenic plant selected in b) with a transgenic plant in which the endogenous diterpene production pathway is blocked in the trichomes. In a particular embodiment, one of the endogenous diterpene synthases is cembratriene-ol synthase.

In a preferred embodiment, the heterologous terpene synthase is a diterpene synthase. Preferably, the diterpene synthase is taxadiene synthase or casbene synthase.

In another preferred embodiment, the heterologous terpene synthase is a monoterpene synthase and the construct additionally comprises a polynucleotide sequence coding for a geranylpyrophosphate synthase under the control of a promoter enabling it to be expressed in the trichomes. Alternatively, the polynucleotide sequence encoding a geranylpyrophosphate synthase can be carried by a second construct different from the first.

In an additional preferred embodiment, the heterologous terpene synthase is a sesquiterpene synthase and the construct additionally comprises a polynucleotide sequence encoding a farnesylpyrophosphate synthase under the control of a promoter enabling it to be expressed in the trichomes. Alternatively, the polynucleotide sequence encoding a farnesylpyrophosphate synthase can be carried by a second construct different from the first.

In yet another preferred embodiment, the heterologous terpene synthase is a triterpene synthase and the construct additionally comprises polynucleotide sequences coding for a farnesylpyrophosphate synthase, a squalene synthase and a squalene epoxidase under the control of a promoter enabling them to be expressed in the trichomes. Alternatively, the polynucleotide sequences encoding the farnesylpyrophosphate synthase, the squalene synthase and the squalene epoxidase can be carried by one or more constructs different from the first.

In a preferred embodiment, the plant having glandular trichomes is a plant from the Asteraceae, Cannabaceae, Solanaceae or Lamiaceae family. Preferably the plant is tobacco, and more particularly *Nicotiana sylvestris*.

In a second aspect, the present invention concerns a plant or seed of a transgenic plant having glandular trichomes, characterized in that the endogenous diterpene production pathway is blocked in the trichomes. More particularly, the endogenous diterpene production pathway can be blocked by blocking the expression of endogenous diterpene synthases. Preferably, the plant having glandular trichomes is a plant from the Asteraceae, Cannabaceae, Solanaceae or Lamiaceae family. Even more preferably, the plant is tobacco, and more particularly *Nicotiana sylvestris*. In a particular embodiment, the endogenous diterpene synthase is cembratriene-ol synthase.

In a third aspect, the invention concerns a transgenic seed or plant having glandular trichomes characterized in that it comprises an expression cassette containing a polynucleotide sequence encoding a heterologous terpene synthase enabling the synthesis of a terpene of interest under the control of a promoter enabling an expression, preferably specific, in the trichomes. Preferably, the expression of the terpene synthase is under the control of a trichome-specific promoter. In a preferred embodiment, said expression cassette comprises at least one enhancer sequence operably linked to the promoter. Preferably, the pathway for producing endogenous diterpenes is blocked in the trichomes of said plant. More particularly, the endogenous diterpene production pathway can be blocked by blocking the expression of the endogenous diterpene synthase. Preferably, the plant having glandular trichomes is a plant from the Asteraceae, Cannabaceae, Solanaceae or Lamiaceae family. Even more preferably, the plant is tobacco, and more particularly *Nicotiana sylvestris*. In a particular embodiment, the endogenous diterpene synthase is cembratriene-ol synthase.

A fourth aspect of the invention relates to the use of a plant according to the invention for producing terpenes of interest.

A fifth aspect of the invention concerns a method for recovering heterologous terpenes in the exudate of the trichomes of a plant, comprising a) harvesting the aerial parts of the plant; b) incubating said aerial parts in a solvent of the low polarity or apolar type; and c) eliminating the solvent.

A sixth aspect of the invention further concerns plants exhibiting an increased efficiency for transformation by bacteria enabling the transfer of DNA into plant cells, and the uses thereof. Thus, the present invention concerns a cell of a plant exhibiting a blocked production of a compound having antibiotic activity at the leaf surface in order to transform said cell with a bacterium enabling DNA transfer into the plant cells. The invention also concerns a method for transforming a plant cell comprising contacting a bacterium enabling DNA transfer into plant cells with a cell of a plant exhibiting a blocked production of a compound having antibiotic activity at the leaf surface. The invention further concerns a method for obtaining transformed plants characterized in that it comprises the following steps: a) obtaining a recombinant bacterial host cell enabling DNA transfer into plant cells comprising a transgene; b) transforming a plant exhibiting a blocked production of a compound having antibiotic properties at the leaf surface, by infection with the recombinant bacterial host cells obtained in step a); c) selecting plants having integrated the transgene in their genome. Preferably, the bacterium belongs to the genus *Agrobacterium*, in particular *Agrobacterium tumefaciens, Rhizobium, Sinorhizobium*, or *Mesorhizobium*. Preferably, the plants are plants having glandular trichomes. In a preferred embodiment, the plant having glandular trichomes is a plant from the Asteraceae, Cannabaceae, Solanaceae or Lamiaceae family. Preferably it is from the Solanaceae family and can be selected from among tobacco, tomato, sunflower and potato. Preferably, the compound having antibiotic activity is a terpene and in particular a diterpene. In particular, the compound is CBT-diol. Preferably, blocking the production of terpenes, in particular of diterpenes such as CBT-diol, is carried out by blocking the expression of endogenous terpene synthases in the trichomes, in particular cembratriene-ol synthase. Blocking can also be carried out by specifically blocking in trichomes the expression of geranylgeranylpyrophosphate synthase (GGPPS), which produces geranylgeranylpyrophopshate, the precursor of all diterpenes.

A seventh aspect of the invention concerns the use of a plant, in which the pathway of endogenous diterpene production, in particular of CBT-diol, is blocked in the trichomes, in order to identify the function of terpenoid biosynthetic genes. More particularly, blocking the CBT-diol production pathway can be carried out by blocking the expression of cembratriene-ol synthase.

DETAILED DESCRIPTION OF THE INVENTION

The inventors have shown that the tobacco *Nicotiana sylvestris* by virtue of its aforementioned metabolic characteristics is an ideal host in which to graft the taxol biosynthetic pathway on the endogenous GGPP pool. More generally, any terpene synthase, and more particularly any diterpene synthase, as long as its coding sequence is known, could be integrated into the tobacco genome in order to yield an abundant production of the diterpenoids which are derived therefrom. This can be generalized for other terpene classes (monoterpenes, sesquiterpenes, or triterpenes for example) to plants having glandular trichomes.

The invention essentially comprises three elements summarized below.

(1) The genetic engineering of tobacco in order to enable de novo expression of the heterologous terpene synthase in the secreting trichomes. The examples described herein are those of taxadiene synthase and casbene synthase which respectively lead to the production of taxadiene and casbene. These examples should not be considered to be limiting of the possibilities for producing diterpenoids by tobacco trichomes. Moreover, the importance of specifically expressing the diterpene synthases in the tobacco trichomes relative to a constitutive expression will be highlighted.

(2) The increase in diterpene production obtained by inhibiting endogenous diterpene synthesis in tobacco. To increase the level of diterpene production by the secreting trichomes, the endogenous diterpene production pathway is blocked at the terpene synthase step. This makes it possible to reduce, if not eliminate, any competition for GGPP, the substrate common to all diterpene synthases. Inactivation of the genes encoding terpene synthase activity (cembratrien-ol synthase in the case of *Nicotiana sylvestris*) is sufficient to virtually eliminate the production of endogenous diterpenes.

(3) The secretion of the diterpenes of interest in the trichome exudate and the recovery of the diterpenoid-containing exudate produced by the trichomes by using a solvent of the low polarity (methylene chloride, chloroform, etc.) or apolar type (eg., pentane, hexane, etc.). Indeed, the inventors have discovered the non-obvious and unforeseeable possibility of secreting terpenes other than endogenous terpenes in the exudate of trichomes.

The inventors have also discovered that plants, in which the production of a compound having antibiotic activity at the leaf surface is blocked, exhibit a higher efficiency of transformation by bacteria enabling DNA transfer into plant cells. In fact, the elimination of CBT-diol production by trichomes at the leaf surface of *N. sylvestris* leads to a highly significant enhancement of the efficiency of genetic transformation by *Agrobacterium tumefaciens*. This can be explained by the antibacterial activity of CBT-diol, which would prevent the growth of *Agrobacterium tumefaciens* and hence the transformation of *N. sylvestris* cells.

Moreover, the inventors have identified several interesting properties of plants in which the CBT-diol synthetic pathway is blocked in the trichomes. In fact, CBT-diol is a major contaminant considering the amounts which are produced. Its presence makes the detection of minor components difficult. Thus, a plant producing little or no CBT-diol facilitates the purification of molecules produced in the trichomes by transgenesis. In addition, such a plant is extremely useful for identifying the function of terpenoid biosynthetic genes. In fact, the low level of CBT-diol in the leaf exudates of such a plant facilitates the "in vivo" identification of the function of genes involved in terpene biosynthesis such as for example terpene synthases, cytochrome P450 monooxygenases, acetyltransferases, benzoyltransferases or N-benzoyltransferases.

The present invention therefore consists in a system for producing terpenes of interest selected in the group consisting of diterpenes, monoterpenes, sesquiterpenes and triterpenes in a plant having glandular trichomes.

In a first embodiment, the invention consists in a system for producing diterpenes of interest, and more particularly taxanes, by glandular trichomes.

Studies of diterpene synthase expression in *Nicotiana sylvestris* show that tobacco trichomes constitute a natural platform suited to the de novo production of diterpenoids, and in particular taxadiene or casbene. The production of taxadiene or casbene in the trichome exudate shows that the trichome secretory system is not specific of a class of diterpenes. In view of a culture for the production of said diterpenes, the specific expression of diterpene synthase in trichomes confers a significant advantage over constitutive expression which is characterized by slower growth.

The choice of tobacco and in particular *Nicotiana sylvestris*, as well as plants having glandular trichomes, is equally adapted for an abundant production of diterpenes. In fact, the expression of taxadiene synthase under the control of a constitutive promoter (35S) in the species *Arabidopsis thaliana* leads to an accumulation of taxadiene which is restricted to the leaves and in small amounts (100 times less than that in *N. sylvestris*) (Besumbes et al., 2004; Botella-Pavia et al., 2004). This difference is related to the physiology of *Arabidopsis thaliana* trichomes which are not glandular.

As shown by the inventors, casbene and taxadiene synthase, which are derived from phylogenetically distant plants (castor oil plant and yew, respectively), are both functional in tobacco trichomes. In light of these observations, the inventors consider that tobacco trichomes constitute a biological factory capable of expressing all kinds of diterpene synthases, regardless of their origins.

The use of a silencing strategy for endogenous terpene synthase genes leads to a significant increase in taxadiene accumulation in the trichomes. Said strategy is therefore particularly adapted to increasing the levels of diterpene production by tobacco trichomes. Generally, silencing the endogenous diterpenoid pathway by any means whatsoever in order to increase the biosynthesis of the grafted genetically engineered pathway represents a clear advantage for producing high yields of diterpenoids of interest.

In a general manner, an expression cassette is composed of a promoter enabling transcription initiation, a transcribed nucleic acid, containing introns or not and whose translation enables the production of a heterologous terpene synthase, and a transcription terminator. The transcribed nucleic acids can be genomic DNA, complementary DNA (cDNA) or synthetic DNA. In the scope of the invention, the transcribed nucleic acids are preferably cDNA devoid of introns. The transcribed nucleic acids can be synthetic or semi-synthetic, recombinant molecules, possibly amplified or cloned into vectors, chemically modified or comprising unnatural bases. Typically they are isolated DNA molecules, synthesized by recombinant methods well known to those skilled in the art. They are typically used in their full length, namely, with the ATG initiation codon of the genes of origin and with their coding sequence for the chloroplast transit peptide. Generally, the diterpene synthases of plants are transported to chloroplasts and therefore possess a transit peptide, whereas the diterpene synthases of organisms which do not possess chloroplasts, such as bacteria or fungi, do not possess a chloroplast transit peptide. In order to correctly express said diterpene synthases in the chloroplasts of plants and in particular of tobacco, it will be necessary to create a fusion with a transit peptide, such as that of the Rubisco small subunit, well known to those skilled in the art.

The term expression cassette designates a nucleic acid construct comprising a coding region and a regulatory region, operably linked. The expression "operably linked" indicates that the elements are combined in such a way that the expression of the coding sequence (the gene of interest) and/or the targeting of the encoded protein are under the control of the transcriptional promoter and/or the transit peptide. Typically, the promoter sequence is placed upstream of the gene of interest, at a distance therefrom which is compatible with control of expression. Similarly, the transit peptide sequence is generally fused upstream of the sequence of the gene of interest, and in frame with it, and downstream of any promoter. Spacer sequences may be present, between the regulatory elements and the gene, as long as they do not prevent expression and/or targeting.

The expression cassette comprises a promoter enabling an expression, preferably specific, in the trichomes of the plant. Such promoters are known to those skilled in the art.

In the spirit of the invention, "specific" promoter shall be understood to mean a promoter which is mainly active in a given tissue or cell group. It shall be understood that a residual expression, generally lower, in other tissues or cells cannot be entirely ruled out. A particular feature of the invention is based on the ability to construct promoters specific of secretory cells of glandular trichomes, enabling a modification of the composition of the leaf secretions of the plant, and in particular enabling the expression therein of the terpene synthase enabling preparation of the terpene of interest.

For example, it has been shown that a 1852 bp regulatory sequence, located upstream of the ATG of the CYP71D16 gene, specifically directs the expression of the uidA reporter gene in the secretory cells of tobacco trichomes (application US 2003/0100050 A1, Wagner et al., 2003). Furthermore, several promoter sequences extracted from different species have been shown to direct the expression of a heterologous gene in tobacco trichomes (Table 1).

Among said promoters, that of the LTP3 gene, coding for a cotton protein involved in lipid transfer (LTP), is specifically expressed in cotton fiber cells. The regulatory sequence of the gene (1548 bp) has been studied in tobacco. Said sequence specifically directs the expression of the uidA gene in leaf trichomes. The 315 bp sequence located between positions −614 and −300 upstream of the ATG is thought to underlie the promoter's specificity. The promoter of the LTP6 gene can also enable trichome-specific expression in cotton. Based on the literature, however, it would appear that the expression occurs in cells at the foot of the trichome, and not in the secretory cells. Moreover, when said promoters are introduced into tobacco, expression is no longer highly specific, with in particular a signal in epidermal cells (see Table 1).

This is why, in a preferred embodiment of the present invention, the promoter used in the cassette is derived from the NsTPS-02a, 02b, 03, and 04 genes of the species *Nicotiana sylvestris* showing high sequence homology with CYC-2 (CBT-ol cyclase; NID: AF401234). The sequence of said promoters is given in SEQ ID Nos. 5 to 8. Thus, the promoter contained in the expression cassette comprises a nucleic acid having functional transcriptional promoter activity in glandular trichomes, characterized in that it comprises all or part of the sequence SEQ ID No: 5, 6, 7 or 8 or a functional variant thereof. More particularly, a functional variant thereof shall be understood to mean a sequence displaying at least 80, 85 or 90% identity with one of said sequences [obtained by blastN sequence alignment software (Altschul et al., 1990)], and is specific of glandular trichomes, in particular of the secretory cells of glandular trichomes. Said promoter sequences are more fully described in patent application FR No. 04 10799 filed on 13 Oct. 2004.

Among terminator sequences, one can cite the NOS terminator (Bevan et al., 1983, Nucleic Acids Res. 11(2), 369-385), and the histone gene terminator (EPO 633 317).

In a particular embodiment, the expression cassette can comprise a sequence enabling increased expression ("enhancer"), for example certain elements of the CaMV35S promoter and of octopine synthase genes (U.S. Pat. No. 5,290,924). Preferably the enhancer of the CaMV35S promoter is used. An example of an enhancer is given in sequence SEQ ID No 9.

The transcribed nucleic acid codes for the terpene synthase capable of synthesizing the terpene of interest.

In a particular embodiment of the invention, the terpene of interest is a diterpene. Preferably, the diterpene of interest is a taxane. More particularly, the taxane can be taxadiene. The heterologous terpene synthase which is introduced into the plant is a diterpene synthase, more particularly the diterpene synthase capable of synthesizing the diterpene of interest. For example, for taxadiene, the diterpene synthase is a taxadiene synthase. More particularly, the taxadiene synthase is that of the yew. FIG. 8 illustrates the strategy for producing taxadiene in tobacco trichomes. Many coding sequences and protein sequences are known for the taxadiene synthase of yew. A non-exhaustive list of references is given below.

| Coding sequence ref. | Protein sequence ref. |
|---|---|
| AY365032 | AAR15329.1 |
| AY364470 | AAR13861.1 |
| AY364469 | AA13860.1 |
| AY461450 | AAS18603.1 |
| U48796 | AAC49310.1 |

Moreover, for casbene, the diterpene synthase is a casbene synthase. More particularly, the casbene synthase is that of the castor oil plant. By way of non-limiting example, one can cite reference L32134 for the coding sequence and reference P59287 for the protein sequence.

More generally, the present invention relates to any diterpene synthase which is known or whose sequence corresponds to the characteristics of diterpene synthases, as indicated hereinbelow.

The genes of several diterpenes synthases have been cloned and their functions confirmed. These include: taxadiene synthase (Wildung and Croteau, 1996), abietadiene synthase (Peters et al., 2000), levopimaradiene synthase (Schepmann et al., 2001), isopimaradiene synthase (Martin et al., 2004), casbene synthase (Mau and West, 1994), cembratriene-ol synthase (Wang and Wagner, 2003), ent-cassadiene synthase (Cho et al., 2004), labdene synthase (Seo et al., 2003), syn-pimaradiene synthase (Wilderman et al., 2004), ent-copalyl diphosphate synthase and ent-kaurene synthase (Sun et al., 1994, Prisic et al., 2004). Other diterpene synthase genes are currently being characterized in rice (syn-stemarene synthase, syn-pimaradiene synthase, ent-sandaracopimaradiene synthase and ent-cassadiene synthase) and tobacco (cis-abienol synthase).

The protein sequences of diterpene synthases share common features. The immature proteins all contain a chloroplast transit peptide at the N-terminal end. All diterpene synthases contain two characteristic domains. The N-terminal domain is called the glycosyl hydrolase-like domain; the C-terminal domain contains the catalytic site.

The diterpene synthases are subdivided into three large classes. Enzymes in class 1 have a DDXXD consensus motif in the C-terminal domain. Enzymes in class II have a (D/E)XD(D/N) consensus motif located in the N-terminal domain (Prisic et al., 2004). Enzymes in classes I and II act sequentially to generate carbon skeletons of the labdane type and are generally characteristic of primary metabolism (eg.: ent-copalyl diphosphate synthase and ent-kaurene synthase), but also participate in secondary metabolism as in rice (eg.: ent-copalyl diphosphate synthase and ent-cassadiene synthase). Other enzymes specific of secondary metabolism in gymnosperms contain these two motifs and are therefore bifunctional with two catalytic sites (eg.: abietadiene synthase). Despite being bifunctional they are listed in class I. All these enzymes (classes I and II) are further characterized by a sequence in the N-terminal domain called CDIS for Conifer Diterpene Internal Sequence. Said sequence is generally about 215 amino acids and is located between the signal peptide and the glycosyl hydrolase-like domain (Trapp and Croteau, 2001).

In angiosperms, enzymes in class III have the DDXXD consensus in the C-terminal region, but not the CDIS of classes I and II. Said enzymes act in a single reaction step. Casbene synthase is an example of a class III diterpene synthase.

The *Arabidopsis thaliana* genome contains 21 sequences which meet the criteria for class III diterpene synthases (Aubourg et al., 2002). Their genomic coordinates, according to the international nomenclature for *Arabidopsis* genes, are as follows: At5g48110, At3g29410, At3 g14490, At1g31950, At4g15870, At2g23230, At1g48800, At1g66020, At3g29110, At1g70080, At1g33750, At3g32030, At3g14520, At3g14540, At5g44630, At4g13280, At4g13300, At4g20210, At3g29190, At4g20230, At4g20200. The proteins encoded by the genes At3g29410, At3g14540, At1g33750, At3g32030 and At1g48800, also have a (D/E)EDD motif of the class II type in the N-terminal domain, which makes them similar to the bifunctional diterpene synthases in class I. Said enzymes can therefore produce labdanoid type diterpenes in a single step. None of the proteins encoded by these sequences has been authenticated. However, the inventors have attempted to characterize two proteins encoded by the genes At3g29410, At3g14540.

In another particular embodiment of the invention, the terpene of interest is a monoterpene. For example, the monoterpene of interest can be limonene. Non-limiting examples are also carene, pinene, thujene, or linalool. The heterologous terpene synthase which is introduced into the plant is a monoterpene synthase, more particularly the monoterpene synthase capable of synthesizing the monoterpene of interest. However, monoterpene production also requires the introduction of a geranylpyrophosphate synthase expressed in trichomes. Non-limiting examples of geranylpyrophosphate synthase are referenced below.

| Organism | Coding sequence ref. | Protein sequence ref. |
|---|---|---|
| Vitis vinifera | AY351862 | AAR08151 |
| Mentha piperata | AF182828 | AAF08793 |
| Abies grandis | AF513112 | AAN01134 |
| Arabidopsis t. | Y17376 | CAC16849 |

FIG. 9 illustrates the strategy for producing monoterpenes in tobacco trichomes. For example, for limonene, the monoterpene synthase is a limonene synthase. Many coding sequences and protein sequences are known for limonene synthase. Non-exhaustive examples of references are given below.

| Coding sequence ref. | Protein sequence ref. |
|---|---|
| AY473624 | AAS47694.1 |
| AF514289 | AAM53946.1 |
| AF514287 | AAM53944.1 |
| AF317695 | AAK06663.1 |
| AF241793 | AAG31438.1 |
| AF241792 | AAG31437.1 |
| AF241791 | AAG61436.1 |
| AF241790 | AAG31435.1 |
| AF233894 | AAF65545.1 |
| AF175323 | AAD50304.1 |

Carene synthase, pinene synthase, thujene synthase, and linalool synthase are other examples of monoterpene synthases.

In another particular embodiment of the invention, the terpene of interest is a sesquiterpene. For example, the sesquiterpene of interest can be valencene, santalene, germacrene or epi-aristolochene.

The heterologous terpene synthase which is introduced into the plant is a sesquiterpene synthase, more particularly the sesquiterpene synthase capable of synthesizing the sesquiterpene of interest. However, sesquiterpene production also requires the introduction of a farnesylpyrophosphate synthase expressed in trichomes.

| Organism | Coding sequence ref. | Protein sequence ref. |
|---|---|---|
| Arabidopsis | L46367 | AAF44787 |
| Artemisia | AY308477 | AAP74720 |
| Mentha | AF384040 | AAK63847 |

FIG. 10 illustrates the strategy for producing sesquiterpenes in tobacco trichomes. For example, for valencene, the sesquiterpene synthase is a valencene synthase. More particularly, the valencene synthase is that of sweet orange. By way of non-limiting example, one can cite reference AF441124 for the coding sequence and reference AAG04608.1 for the protein sequence.

Germacrene synthase (SSTLH1 gene, reference AF279455) and epi-aristolochene synthase (reference AAA19216) are other examples of sesquiterpene synthases.

In another particular embodiment of the invention, the terpene of interest is a triterpene. For example, the triterpene of interest can be lanosterol, cycloartenol, lupeol or beta-amyrin.

The heterologous terpene synthase which is introduced into the plant is a triterpene synthase, more particularly the triterpene synthase capable of synthesizing the triterpene of interest. However, triterpene production also requires the introduction of a farnesylpyrophosphate synthase, a squalene synthase, and squalene epoxidase expressed in trichomes.

| Enzyme | Coding sequence ref. | Protein sequence ref. |
|---|---|---|
| Squalene synthase | D29017 | BAA06103 |
| Squalene epoxidase | NM_104624 | NP_564734 |

FIG. 11 illustrates the strategy for producing triterpenes in tobacco trichomes. For example, for lanosterol, the triterpene synthase is a lanosterol synthase. Many coding sequences and protein sequences are known for lanosterol synthase.

Lanosterol synthase, cycloartenol synthase, lupeol synthase and beta-amyrin synthase are other examples of triterpene synthases.

In addition to the introduction of a construct containing an expression cassette comprising a polynucleotide sequence encoding a heterologous terpene synthase, the method can comprise the introduction into the plant cell of one or more transgenes each encoding a terpene modification enzyme. In particular, the terpene modification can be a hydroxylation, an acylation and in particular an acetylation, a benzoylation, a dehydrogenation, etc. The introduction of the transgene preferably takes place by introducing an expression cassette comprising a polynucleotide sequence encoding a terpene modification enzyme. The polynucleotide sequence encoding a terpene modification enzyme is under the control of a promoter enabling expression in trichomes, preferably trichome-specific. The transgene can be carried by the construct comprising the polynucleotide sequence encoding a heterologous terpene synthase or by a different construct. For example, said modification enzyme can be a P450 monooxygenase, an acyltransferase, a benzoyltransferase, a reductase, among others. A non-exhaustive list of genes coding for terpene modification enzymes is given in the following table.

| Enzyme | Gene (Genbank accession No.) | Terpene skeleton modified |
|---|---|---|
| Taxoid 2-alpha hydroxylase | AY518383 | Taxadiene |
| Taxadiene 5-alpha hydroxylase | AY289209 | Taxadiene |
| Taxoid 7-beta hydroxylase | AY307951 | Taxadiene |
| Taxoid 10-beta hydroxylase | AY563635 | Taxadiene |
| 5-alpha-taxadienol-10-beta-hydroxylase | AY453403 | Taxadiene |
| Taxane 14b-hydroxylase | AY188177 | Taxadiene |
| Taxane 13-alpha-hydroxylase | AY056019 | Taxadiene |
| Taxane hydroxylase | AY374652 | Taxadiene |
| Taxadien-5-alpha-ol-O-acetyl-transferase | AY628434 | Taxadiene |
| Taxadienol acetyl transferase | AF190130 | Taxadiene |
| 10-deacetylbaccatin III-10-O-acetyl transferase | AF193765 | Taxadiene |
| 2-debenzoyl-7,13-diacetylbaccatin III-2-O-benzoyl transferase | AF297618 | Taxadiene |
| 3'-N-debenzoyltaxol N-benzoyl-transferase | AF297618 | Taxadiene |
| Taxoid phenylpropanoyltransferase | AY082804 | Taxadiene |
| Taxane 2-alpha-O-benzoyltransferase | AY675557 | Taxadiene |
| Taxoid-O-acetyltransferase | AY628433 | Taxadiene |
| 5-epi-aristolochene-1,3-dihydroxylase | AF368376 | 5-epi-aristolochene |
| Abietadienol/abietadienal oxidase | AY779538 | Abietadiene, dehydroabietadiene, levopimaradiene, isopimaradiene |
| Limonene-3-hydroxylase | AAQ18708 | Limonene |
| (−)-isopiperitenol dehydrogenase | AY641428 | Limonene |
| (−)-isopiperitenone reductase | AY300162 | Limonene |
| (+)-pulegone reductase | AY300163 | Limonene |
| Menthol dehydrogenase | AY288138 | Limonene |

The expression cassette so formed is inserted in a vector. The vector can be DNA or RNA, circular or not, single- or double-stranded. Typically it is a plasmid, phage, virus, cosmid, artificial chromosome, etc. Advantageously it is a plant vector, that is to say, capable of transforming a plant cell. Examples of plant vectors are described in the literature, including in particular the *A. tumefaciens* T-DNA plasmids pBIN19 (Bevan, 1984), pPZP100 (Hajdukewicz et al., 1994), pCAMBIA series (R. Jefferson, CAMBIA, Australia). The vectors of the invention can additionally comprise an origin of replication and/or a selection gene and/or a plant recombination sequence, etc. The vectors can be constructed by conventional molecular biology methods, well known to those skilled in the art, using for example restriction enzymes, ligation, clonings, replication, etc.

The selection genes comprise, in a non-exclusive manner, the use of marker genes such as genes conferring resistance to an antibiotic or to herbicides, or positive selection systems, in particular the system based on selection on mannose, in the presence of the MPI selection gene (mannose-6-phosphate isomerase) (Hansen and Wright, 1999), or selection systems coupled to elimination of the marker genes after selection (Ebinuma et al., 1997). Finally, the transformed plants can also be selected by PCR screening in the absence of selectable marker genes (McGarvey and Kaper, 1991).

Introduction of the inventive constructs into a plant cell or tissue, including a seed or plant, can be carried out by any method known to those skilled in the art, and comprise for example the use of the bacterium *Agrobacterium tumefaciens*, electroporation, conjugative transfer, gene gun methods, transfection with a viral vector in particular, and any other method known to those skilled in the art.

A commonly used method is based on the use of the bacterium *Agrobacterium tumefaciens*, which mainly consists in introducing the construct of interest (nucleic acid, cassette, vector, etc.) in the bacterium *A. tumefaciens*, then contacting said bacterium with the leaf discs of the chosen plant. The expression cassette is typically introduced in the bacterium by using as vector the Ti plasmid (or T-DNA), which can be transferred into the bacterium for example by heat shock. Incubation of the transformed bacteria with leaf discs leads to transfer of the Ti plasmid into the genome of the disc cells. The latter can optionally be cultivated in suitable conditions in order to regenerate a transgenic plant the cells of which comprise the construct of the invention. For further details or variant implementations of the *A. tumefaciens* transformation method, reference can be made to Horsch et al., 1985 or Hooykaas and Schilperoort, 1992 for example.

Thus, in a particular embodiment, the expression cassette so formed is inserted between the left and right borders of the transfer DNA (T-DNA) of a disarmed Ti plasmid for transfer into plant cells by *Agrobacterium tumefaciens*. The T-DNA also comprises a gene whose expression confers resistance to an antibiotic and which enables the selection of transformants.

Another method of plant transformation is based on projecting microparticles (typically microbeads) to which gene constructs are attached, directly on plant cells, then culturing said cells in order to reconstitute a transgenic plant. The particles which are used are typically gold particles, which are typically projected by means of a particle gun (see in particular Russell et al., In Vitro Cell. Dev. Biol., 1992, 28P, p. 97-105).

The microinjection method is based primarily on injecting the gene constructs into plant protoplasts or embryos, then cultivating said tissues so as to regenerate whole plants. Other plant transgenesis methods are well known, or other protocols implementing the above methods are described in the prior art (Siemens, J and Schieder, 1996) and can be employed in the invention.

In particular the present invention can be used for producing terpenes of interest specifically in the secretory cells of glandular trichomes of higher plants (in particular the Angiosperms). The invention is applicable in particular to all the plants from families having glandular trichomes, for example Asteraceae (sunflower, etc.), Solanaceae (tomato, tobacco, potato, pepper, eggplant, etc.), Cannabaceae (eg., *Cannabis sativa*) and Lamiaceae (mint, basil, lavender, thyme, etc). The invention is particularly adapted to plants from the Solanaceae family, such as for example the genuses *Solanum, Lycopersicon, Capsicum, Petunia, Datura, Atropa,* etc., and to Nicotianeae, for example tobacco, and more particularly the wild tobacco *Nicotiana sylvestris*. In a non-limiting manner, the invention can be applied to plants from the following genuses: *Populus, Lycopersicon, Nicotiana, Cannabis, Pharbitis, Apteria, Psychotria, Mercurialis, Chrysanthemum, Polypodium, Pelargonium, Mimulus, Matricaria, Monarda, Solanum, Achillea, Valeriana, Ocimum, Medicago, Aesculus, Plumbago, Pityrogramma, Phacelia, Avicennia, Tamarix, Frankenia, Limonium, Foeniculum, Thymus, Salvia, Kadsura, Beyeria, Humulus, Mentha, Artemisia, Nepta, Geraea, Pogostemon, Majorana, Cleome, Cnicus, Parthenium, Ricinocarpos, Hymennaea, Larrea, Primula, Phacelia, Dryopteris, Plectranthus, Cypripedium, Petunia, Datura, Mucuna, Ricinus, Hypericum, Myoporum, Acacia, Diplopeltis, Dodonaea, Halgania, Cyanostegia, Prostanthera, Anthocercis, Olearia, Viscaria.*

Once regenerated, the transgenic plants can be tested for expression of the heterologous terpene synthase or for production of the terpene of interest in the trichomes. This can be done by collecting the leaf exudate and testing for the presence of the terpene of interest in said exudate, when the terpene of interest is meant to be secreted. This can also be done by analyzing the presence of the heterologous terpene synthase in the leaves and, more particularly, in the trichome cells (for example by analyzing mRNA or genomic DNA with specific primers or probes). Optionally the plants can be selected, crossed, treated, etc. in order to obtain plants displaying improved levels of expression.

In this regard, another object of the invention is based on a modified cell comprising a cassette or a vector such as defined hereinabove. For example it can be a plant cell, in particular from the Solanaceae, Asteraceae, Cannabaceae or Lamiaceae family. The cells can be cultivated in vitro, and used to reconstitute tissues or whole plants, in order to produce terpenes of interest in culture, or else to study the properties of heterologous terpene synthases (for example by functional genomics).

Another object of the invention is also based on a plant or seed comprising an expression cassette or a vector such as defined hereinabove. More particularly, the invention relates to a transgenic seed or plant having glandular trichomes and comprising an expression cassette containing a polynucleotide sequence encoding a heterologous terpene synthase enabling the synthesis of a terpene of interest under the control of a promoter enabling an expression, preferably specific, in the trichomes. When the terpene synthase is a monoterpene synthase, the transgenic seed or plant additionally comprises an expression cassette containing a polynucleotide sequence encoding a geranylpyrophosphate synthase under the control of a promoter enabling it to be expressed in the trichomes. When the terpene synthase is a sesquiterpene synthase, the transgenic seed or plant additionally comprises an expression cassette containing a polynucleotide sequence encoding a farnesylpyrophosphate synthase under the control of a promoter enabling it to be expressed in the trichomes. When the terpene synthase is a triterpene synthase, the transgenic seed or plant additionally comprises an expression cassette containing a polynucleotide sequence coding for a farnesylpyrophosphate synthase, a squalene synthase and a squalene epoxidase under the control of a promoter enabling them to be expressed in the trichomes.

In a preferred embodiment of the invention, the plant additionally exhibits a blocked endogenous terpene production pathway in the trichomes. In a preferred embodiment, the endogenous terpene production pathway is specifically blocked in the trichomes, meaning that it is hardly if at all affected in the other parts of the plant. The endogenous terpene production pathway is preferably blocked by blocking the expression of endogenous terpene synthases. However, the invention also provides for blocking the pathway for producing endogenous terpenes at another level.

The expression of endogenous terpene synthases can be blocked by many available techniques known to those skilled in the art. The terpene synthase genes can be deleted, mutated (for eg., chemical mutation by EMS or irradiation) or interrupted (insertional mutagenesis). Furthermore, the expression of endogenous terpene synthases can also be blocked by gene silencing by expressing a transcript inhibitor. The transcript inhibitor is an RNA which can take the form of a double-stranded RNA, an antisense RNA, a ribozyme, an RNA which can form a triple helix, and which has some complementarity or specificity with the transcript of the endogenous diterpene.

According to a particular embodiment of the present invention, the transcript inhibitor is in the form of an antisense RNA. The latter generally comprises a nucleotide sequence complementary to at least a part of the transcript of endogenous terpene synthases, and selectively hybridizes with said transcripts via classical Watson-Crick type interactions. The transcript inhibitor(s) of the antisense RNA type can therefore bind to the transcripts of the terpene synthases and for example block access to the cellular translation machinery at the 5' end of the transcript of interest when the latter is an mRNA, hinder the translation thereof into protein, and enable the suppression of expression of the transgene of interest in vivo (Kumar et al., Microbiol. Mol. Biol. Rev, 62 (1993) 1415-1434). For example such polynucleotides are described in patents EP 92574 and EP 140308. When the transcript inhibitor is of the antisense RNA type, it can cover all or part of the coding sequence of the diterpene synthase transcript, or all or part of the 3' or 5' noncoding sequence. In a preferred manner, the antisense transcript inhibitor is complementary to the ribosome binding and translation initiation sequence. In a preferred manner, the transcript inhibitor has a length of at least 10 ribonucleotides.

In a preferred embodiment, the transcript inhibitor makes use of the mechanism of RNA interference (reviewed in Baulcombe, 2004). Preferably, said silencing is carried out by the intron-spliced hairpin RNA or ihpRNA method (Smith et al., 2000). This consists in producing a double-stranded RNA of the target gene(s) by means of a construct comprising a sense fragment and this same fragment in the antisense orientation, the two being separated by an intron (Wesley et al., 2001; Wang et al., patent application, 1999). Said construct is preferably under the control of a promoter enabling trichome-specific expression.

However, the present invention also considers any means known to those skilled in the art for blocking the endogenous terpene production pathway in trichomes. In fact, it is important to specify that the TPS gene silencing method can be accomplished by other approaches. For example, it can consist in creating a library of deletion mutants by irradiation, for example with gamma rays or fast-neutron radiation. The deletions affecting a given locus can be detected by various methods on the DNA extracted from the mutants (Tissier & Montanë, 1999). One advantage of radiation mutagenesis is the possibility of isolating deletions covering an entire gene cluster. This is particularly relevant in the case of the cembrane synthases of *Nicotiana*, since the genes encoding these enzymes form a family of very similar genes clustered on one locus (Tissier et al., 2004; Sallaud et al., unpublished data).

The present invention also concerns a transgenic seed or plant according to the invention additionally comprising a transgene coding for a terpene modification enzyme.

In particular the invention concerns a plant in which the endogenous diterpene synthesis pathway is blocked in the trichomes. Said plant represents an important intermediate for preparing the final plant capable of producing the terpene of interest. In fact, said plant can be obtained by crossing a plant capable of producing the terpene of interest with a plant in which the endogenous diterpene synthesis pathway is blocked in the trichomes. More particularly, then, the invention concerns a plant in which the endogenous diterpene synthesis pathway is blocked in the trichomes. The invention also concerns the use of a transgenic plant in which the endogenous diterpene synthesis pathway is blocked in the trichomes for preparing a transgenic seed or plant comprising an expression cassette containing a polynucleotide sequence encoding a heterologous terpene synthase enabling the synthesis of a terpene of interest under the control of a promoter enabling an expression in the trichomes. The invention further concerns a method for preparing a transgenic seed or plant in which the endogenous diterpene synthesis pathway is blocked in the trichomes and which is capable of producing a terpene of interest comprising crossing a transgenic plant in which the endogenous diterpene synthesis pathway is blocked in the trichomes with a transgenic plant comprising an expression cassette containing a polynucleotide sequence encoding a heterologous terpene synthase enabling the synthesis of a terpene of interest under the control of a promoter enabling an expression in the trichomes.

Yet another object of the invention is a method for obtaining transformed plants characterized in that it comprises the following steps: a) obtaining a recombinant plant host cell comprising an expression cassette according to the invention; b) regenerating a whole plant from the recombinant host cell obtained in step a); c) selecting plants obtained in step b) having integrated an expression cassette such as defined herein.

The invention also has as object a method for obtaining a transformed plant characterized in that it comprises the following steps: a) obtaining a recombinant host cell of *Agrobacterium tumefaciens* according to the invention; b) transforming a plant of interest by infection with *Agrobacterium tumefaciens* recombinant host cells obtained in step a); c) selecting plants having integrated into their genome an expression cassette such as defined herein.

The invention also has as object a method for obtaining a transformed plant characterized in that it comprises the following steps: a) transfecting at least one plant cell with an expression cassette or with a recombinant vector according to the invention; b) regenerating a whole plant from the recombinant plant cell obtained in step a); c) selecting plants having integrated into their genome an expression cassette according to the invention.

Any one of the foregoing methods for obtaining a transformed plant can also comprise the following additional steps: d) crossing two transformed plants such as obtained in step c) with a plant of the same species; e) selecting plants that are homozygous for the transgene.

In a second particular embodiment, any one of the foregoing methods for obtaining a transformed plant can also comprise the following additional steps: f) crossing a transformed plant obtained in step c) with a plant of the same species; g) selecting plants resulting from the cross in step f) having conserved the transgene.

The hybrid transgenic plants, obtained by crossing at least one plant according to the invention with another, are also part of the invention.

Lastly, the present invention concerns a method for recovering heterologous terpenes or terpenes of interest in the trichome exudate of a plant, comprising a) harvesting the aerial parts of the plant; b) incubating said aerial parts in a solvent of the low polarity or apolar type; and c) eliminating the solvent. Preferably, said plant is a transgenic plant according to the invention and in particular tobacco. Aerial parts shall be understood to mean preferably the leaves and stems. The low polarity solvent can be methylene chloride or chloroform. In a particular embodiment, the solvent is apolar, preferably very apolar. For example, the solvent can be pentane or hexane or any solvent having the same polarity, preferably pentane. The incubation step can last from a few seconds with shaking to several hours in a bath without shaking. Preferably, the chosen solvent is volatile at room temperature and is chemically inert towards the terpenes of interest. Preferably, the solvent is eliminated by evaporation thereof. However, any method whereby the solvent is eliminated is encompassed in the invention.

Moreover, the inventors have discovered that plants, in which the production of a compound having antibiotic properties at the leaf surface is blocked, display an enhanced efficiency of transformation by a bacterium enabling DNA transfer into plant cells. The compound can have antibacterial properties. In a preferred embodiment, the blocked production of the compound is specific of the trichomes.

In fact, terpenes, particularly those secreted at the leaf surface, are compounds which often have antibiotic activity (see for example the references: Trombetta et al., 2005; Chorianopoulos et al., 2004; Friedman et al., 2004; Rios & Recio, 2005; Saroglou et al., 2005). Consequently, the presence of said terpenes having antibiotic activity represents an obstacle to the transformation of said plants by bacteria used for this purpose, in particular of the genus *Agrobacterium, Rhizobium, Mesorhizobium* or *Sinorhizobium* (Broothaerts et al., 2005). This is because said molecules will inhibit the proliferation of the bacteria during transformation and thereby inhibit DNA transfer into the plant cells. As a result, the elimination of said terpenes having antibiotic activity could either make it possible to transform recalcitrant species, or increase the transformation frequencies of hard-to-transform species.

Preferably, said bacterium belongs to the genus *Agrobacterium*, in particular *Agrobacterium tumefaciens, Rhizobium, Sinorhizobium* or *Mesorhizobium*.

The compound having antibiotic properties can be a terpene. For example, it can be a diterpene. In a preferred embodiment, the compound is CBT-diol. In this case, the production of this terpene can be blocked by blocking the expression of endogenous terpene synthases in the trichomes, in particular a diterpene synthase, preferably cembratriene-ol synthase. The means available to carry out this block have been described in detail hereinabove. In particular, these include physicochemical mutagenesis of the gene, deletion of the gene, insertional mutation thereof or "gene silencing". The latter method is preferred.

Alternatively, the compound having antibiotic properties can be one of the following compounds, the list of which is not exhaustive: α-pinene, myrcene, ocymene, α-terpinene, p-cymene, carvacrol, thymol, linalool, camphor, terpineol, β-caryophyllene, caryophyllene oxide, patchoulol, germacrenes (A, B, C or D), β-selinene, cadinene, bisabolenes (α, β, γ), bisabolol, santalenes (α et β), santalols, etc., but also the sesquiterpene lactones present in many Asteraceae species.

The present invention therefore relates to the use of one such transgenic plant for transforming said plant with a bacterium enabling DNA transfer into plant cells. The invention also relates to a method for transforming a plant, said plant exhibiting a blocked production of a compound having antibiotic properties at the leaf surface, comprising contacting a bacterium enabling DNA transfer into plant cells and carrying a transgene with a cell of said plant. Preferably, the cell of said plant is comprised in a leaf fragment, in particular a leaf disc. Yet another object of the invention is a method for obtaining transformed plants characterized in that it comprises the following steps: a) obtaining a recombinant host cell of a bacterium enabling DNA transfer into plant cells comprising a transgene, preferably *Agrobacterium tumefaciens*; b) transforming a plant exhibiting a blocked production of a compound having antibiotic properties at the leaf surface by infection with the recombinant bacterial host cells obtained in step a); c) selecting plants having integrated the transgene into their genome. The foregoing method for obtaining a transformed plant can also comprise the following additional steps: d) crossing two transformed plants such as obtained in step c) with a plant of the same species; e) selecting plants that are homozygous for the transgene. In addition, the method can comprise the following additional steps: f) crossing a transformed plant obtained in step c) with a plant of the same species; g) selecting plants resulting from the cross in step f) having conserved the transgene The present invention concerns the use of a plant, in which the pathway for producing endogenous diterpenes, in particular CBT-diol, is blocked in the trichomes, for identifying the function of terpenoid biosynthetic genes. More particularly, the CBT-diol production pathway can be blocked by blocking the expression of cembratriene-ol synthase.

Other aspects and advantages of the invention will become apparent in the following examples, which are given for purposes of illustration and not by way of limitation.

The patent or application file contains at least one drawing executed in color. Copies of this patent or patent application publication, with color drawing(s), will be provided by the Office upon request and payment of the necessary fee.

DESCRIPTION OF FIGURES

The patent or application file contains at least one drawing executed in color. Copies of this patent or patent application publication, with color drawing(s), will be provided by the Office upon request and payment of the necessary fee.

FIG. 13.

EXAMPLES

Figure 1:
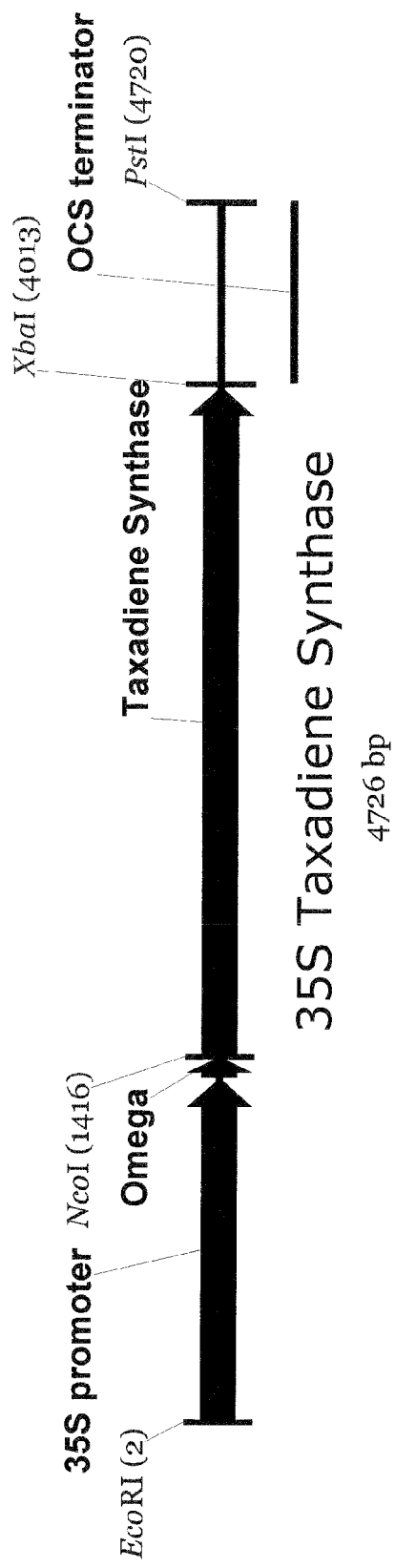
FIG. 1: Non-specific taxadiene synthase expression cassette in cells of tobacco.
Figure 2:
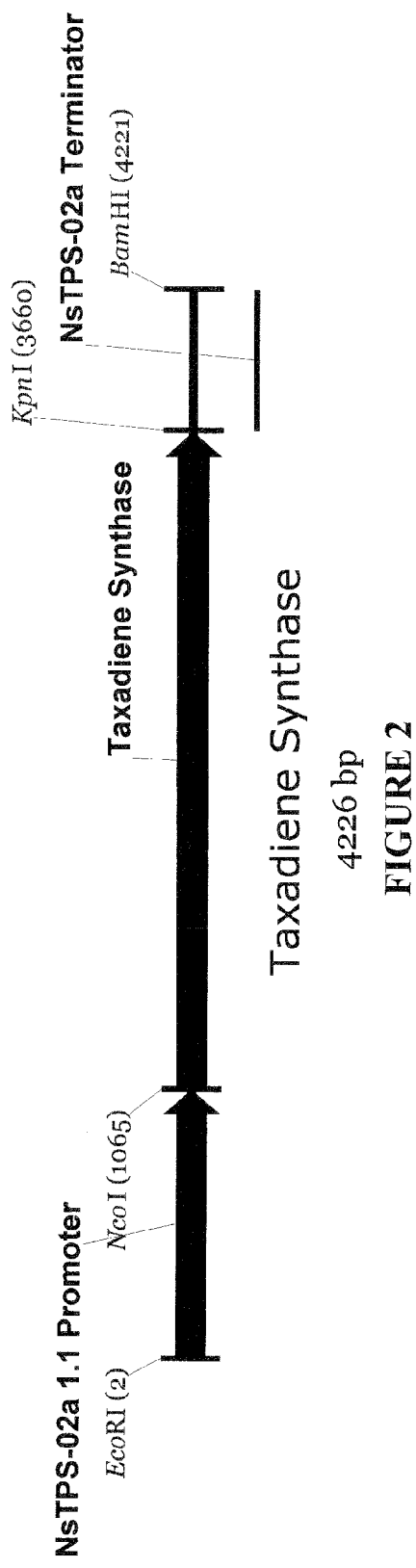
FIG. 2: Taxadiene synthase expression cassette in tobacco trichomes.
Figure 3:
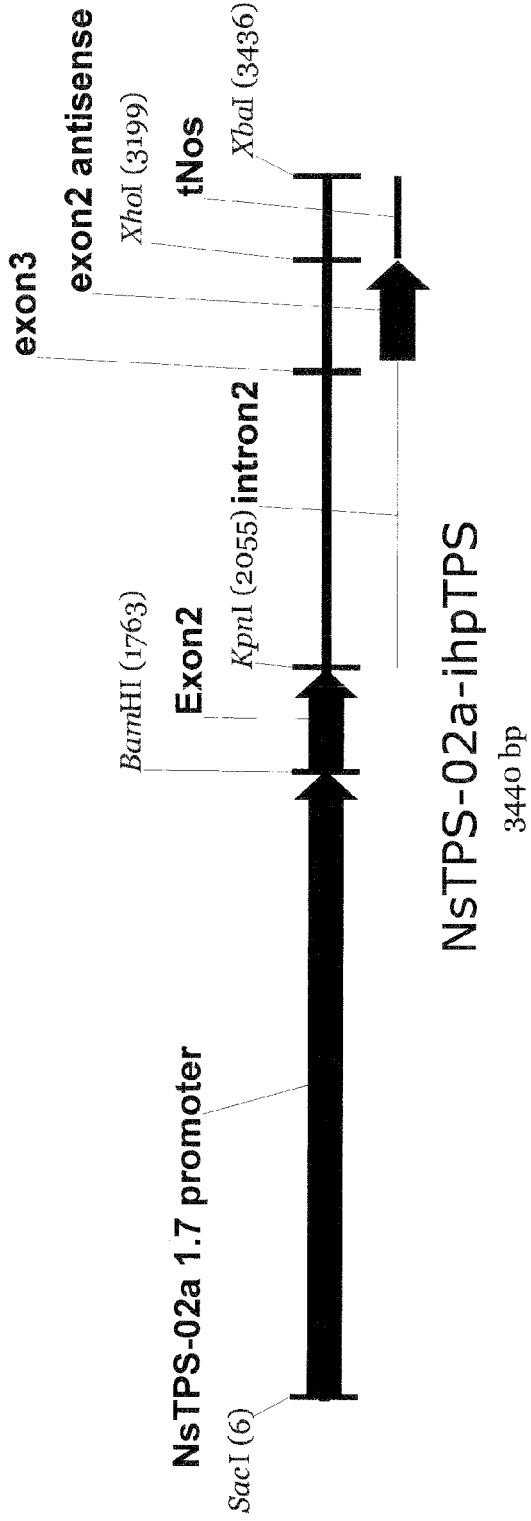
FIG. 3: RNAi construct for NsTPS gene silencing.
Figure 5:
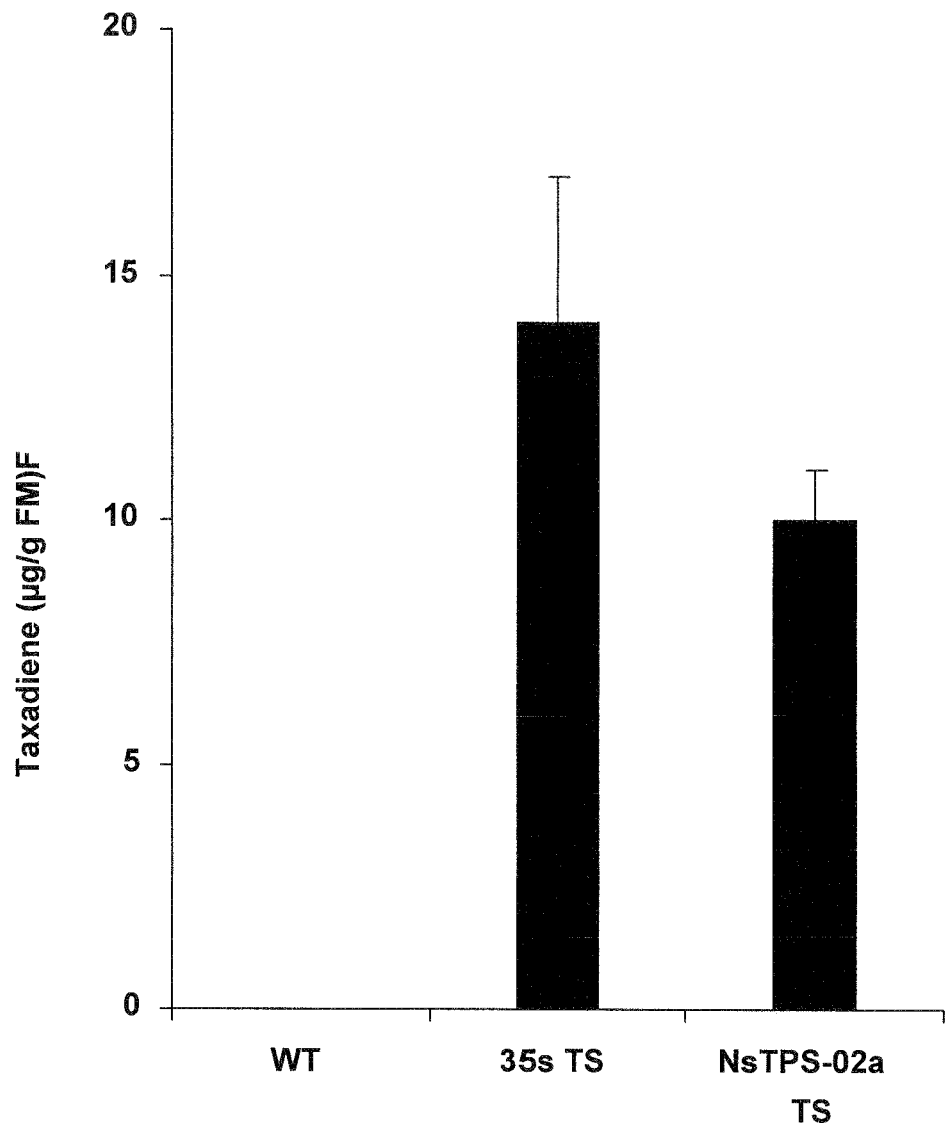
FIG. 5: Taxadiene secretion in lines expressing taxadiene synthase under the control of the 35S or NsTPS-02a promoter. The constructs with 35S or NsTPS-02a promoter controlling taxadiene synthase expression, were cloned into the genome of *Nicotiana sylvestris*. Taxadiene secreted in the exudate of plants carrying a single copy of the transgene was extracted with pentane and quantified by GC-MS. The taxadiene content is expressed in µg/g of fresh matter. A total of 12 and 5 plants were analysed for the $^{35}$S and NsTPS-02a promoter, respectively. (TS: Taxadiene Synthase, WT: Wild Type)
Figure 6:
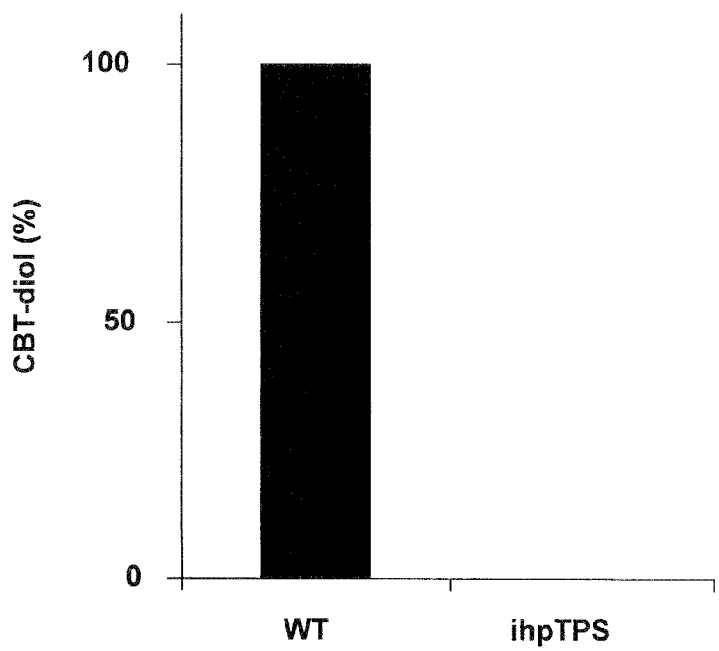
FIG. 6: CBT-diol secretion in plants expressing the ihpTPS RNAi. CBT-diol was extracted from *Nicotiana sylvestris* exudate with pentane and quantified by GC-MS. The CBT-diol content was set at 100% for WT. Plants (Ti) originating from the descendants of transformants are represented by ihpTPS.

Production of Taxadiene in the Tobacco Plant *Nicotiana sylvestris* by Expression of Taxadiene Synthase Under the Control of a Non-Specific Promoter The constructs described below enabled an expression in all the cells of the plant, including in the trichomes. Said expression is described as non-specific of trichomes.
Expression Vector
The expression cassette was constructed as follows (see diagram in FIG. 1):
A constitutive promoter of the type 35S (extracted from cauliflower mosaic virus) well known to those skilled in the art.
Taxadiene synthase cDNA.
The OCS terminator (extracted from octopine synthase gene of an *Agrobacterium tumefaciens* Ti plasmid) well known to those skilled in the art.
The sequence of this construct is given in sequence SEQ ID No 1.
Analysis of Transformed Plants
The regeneration process led to the isolation of transgenic plants expressing taxadiene synthase. Plants containing a single copy of the transgene were selected and analysed by gas chromatography coupled to mass spectrometric detection (GC-MS). The exudate of said plants contained 14±3 µg/g of FM (fresh matter) (FIG. 5). The growth of these plants was slower than the wild-type control (non-transformed) making it unsuitable for culture. These effects have previously been observed in the case of diterpene synthase overexpression in the tomato or *Arabidopsis thaliana* and are attributed to the decrease in the available GGPP pool in transgenic plants (Fray et al., 1995; Besumbes et al., 2004). GGPP is an important metabolite in the synthesis of hormones such as the gibberellins and abscisic acid.
Trichome-Specific Production of Taxadiene in the Tobacco *Nicotiana sylvestris*.
In this example, taxadiene synthase was placed under the control of the trichome-specific promoter NsCBTS-02a (Tissier et al., 2004; patent No. FR 0410799) so as to restrict the production of taxadiene to the trichomes.
Expression Vector
The expression cassette was constructed as follows (see diagram in FIG. 2):
The 1 kilobase NsCBTS-02a promoter.
Taxadiene synthase cDNA.
The NsCBTS-02a gene terminator
The sequence of this construct is given in sequence SEQ ID No 2.
Analysis of Transformed Plants
The regeneration process led to the isolation of transgenic tobacco plants expressing taxadiene synthase specifically in the trichome secretory cells. Plants containing a single copy of the transgene were selected. GC-MS analysis of the exudate revealed a taxadiene content similar to that measured in the case of non-specific expression of taxadiene synthase under control of the 35S promoter (10±1 µg/g of FM, FIG. 5). The growth of these plants was identical to that of the wild-type (non-transformed) plants. Moreover, the flowers had normal fertility. This shows that the trichome-specific synthesis of taxadiene did not have any deleterious effect on the plant, and therefore demonstrates the superiority of trichome-specific expression over non-specific expression.
Increased Taxadiene Production in *Nicotiana sylvestris* Trichomes by Inhibition of Expression of NsCBTS Genes
The NsCBTS genes were inactivated by gene silencing, which involves the mechanism of RNA interference (reviewed in Baulcombe, 2004). Silencing was carried out by the intron-spliced hairpin RNA or ihpRNA method (Smith et al., 2000). It consists in producing a double-stranded RNA of the target gene or genes by means of a construct comprising a sense fragment and this same fragment in the antisense orientation, the two fragments being separated by an intron (Wesley et al., 2001; Wang et al., patent application 1999). More specifically, the cassette was constructed as follows (FIG. 3):
A 1.7 kb fragment of the NsCBTS-02a promoter (patent No. FR 0410799).
A fragment comprising exon 2 and intron 2 of the NsCBTS-02a gene followed by exon 2 of this same gene in the antisense orientation.
The NOS terminator.
Transformation of said cassette by *Agrobacterium tumefaciens* yielded transgenic plants expressing the ihpRNA construct for the CBTS genes. Plants containing a single copy of the transgene were selected. The descendants of these plants were analysed for CBT-diol content. FIG. 6 shows that CBT-diol secretion was almost completely blocked in ihpTPS plants (0.1 to 1% of WT).
Said plants were then crossed with plants expressing taxadiene synthase specifically in the trichomes (see hereinabove). In the descendants of this cross, plants carrying both constructs were selected on selective media and analysed for taxadiene content by GC-MS.
Taxadiene production in these plants was approximately 30 times higher than in plants expressing only the taxadiene expression cassette under the control of a trichome-specific promoter.

Trichome-Specific Production of Casbene in the Tobacco *Nicotiana sylvestris*.

Expression Vector

Figure 4:
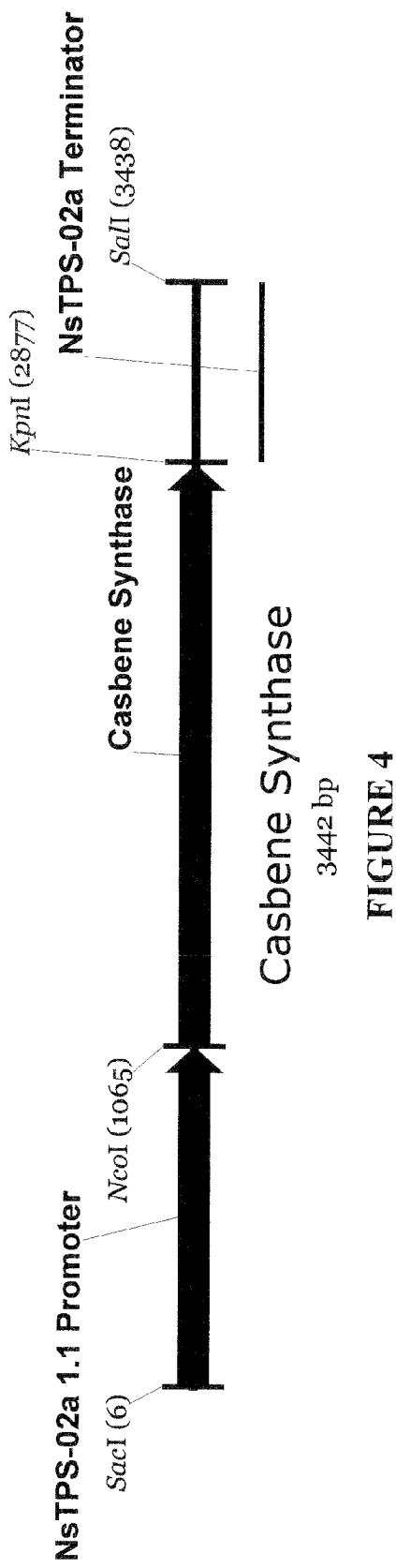
FIG. 4: Casbene synthase expression cassette in tobacco trichomes.

Trichome-specific expression of casbene synthase required the use of the specific promoter NsCBTS-02a in an expression cassette as follows (FIG. 4: diagram and sequence):

The 1 kilobase NsCBTS-02a promoter.
The complete cDNA of casbene synthase.
The NsCBTS-02a terminator Analysis of Transformed Plants The regeneration process led to the isolation of transgenic plants expressing casbene synthase specifically in the trichome secretory cells. GC-MS analysis of plants containing a single copy of the transgene revealed a casbene content of approximately 15 μg/g of FM. The growth of these plants was identical to that of wild-type (non-transformed) plants. This confirms, as for taxadiene, that the specific synthesis of casbene synthase in trichomes has no deleterious effect on the plant.

Increased Expression of a Transgene by Using a 35S Transcriptional Activator (Enhancer)

Figure 7:
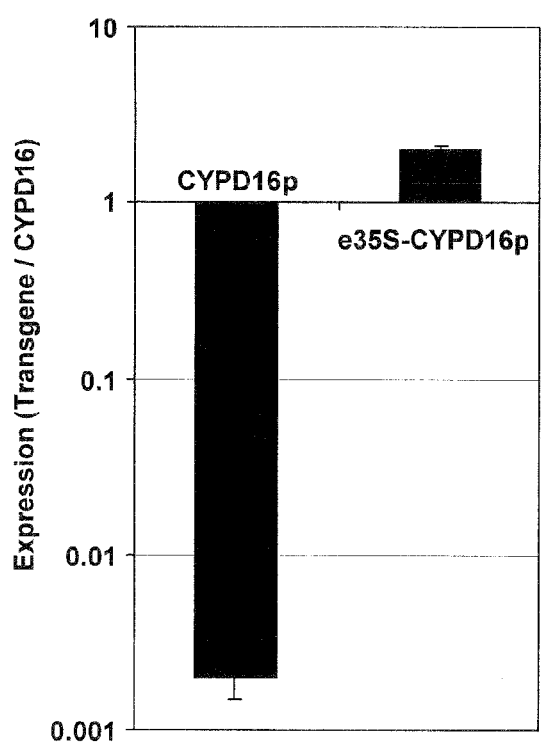
FIG. 7: Effect of 35S promoter enhancer on expression in the trichomes. Total RNA from tobacco leaves (*N. Sylvestris*) was extracted and converted to complementary DNA by reverse transcription. The expression ratio was determined by quantitative duplex PCR (VIC fluorophore for CYP71D16 and FAM for the transgene). N=5 plants were analysed. (e35S: enhancer of promoter 35S, p: promoter).
Figure 8:
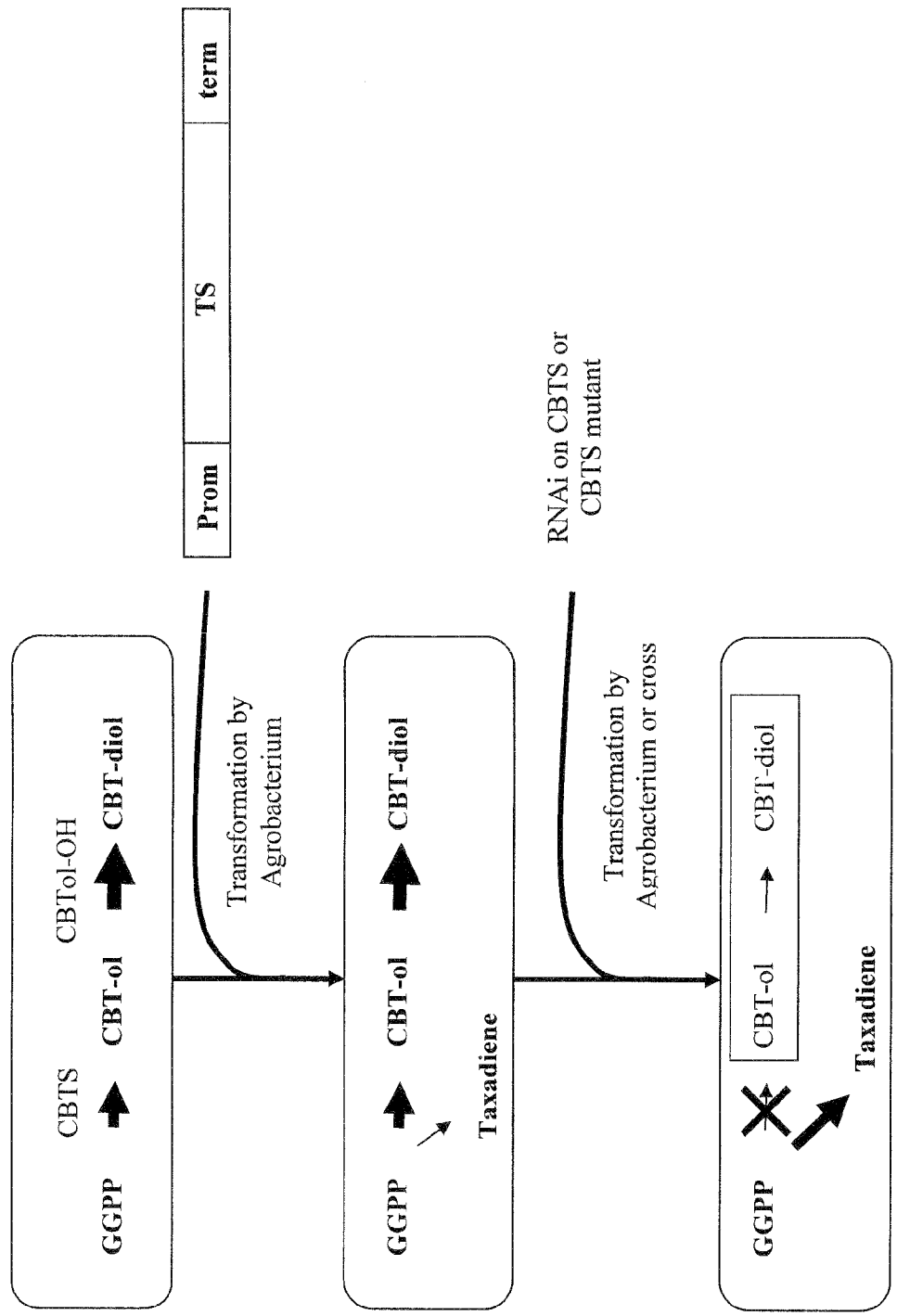
FIG. 8: Outline of the steps leading to taxadiene production in tobacco trichomes (*Nicotiana sylvestris*). GGPP: geranylgeranyl pyrophosphate; CBT-ol: cembratriene-ol; CBT-diol: cembratriene-diol; CBTS: cembratriene-ol synthase; CBTol-OH: cembratriene-ol hydroxylase. Prom: designates a promoter enabling expression in trichomes, preferably in a specific manner. TS: taxadiene synthase; term: transcription terminator. CBTS RNAi: designates a tobacco plant in which the genes enabling CBTS synthesis have been silenced by a construct of the ihpRNA type (see example).
Figure 9:
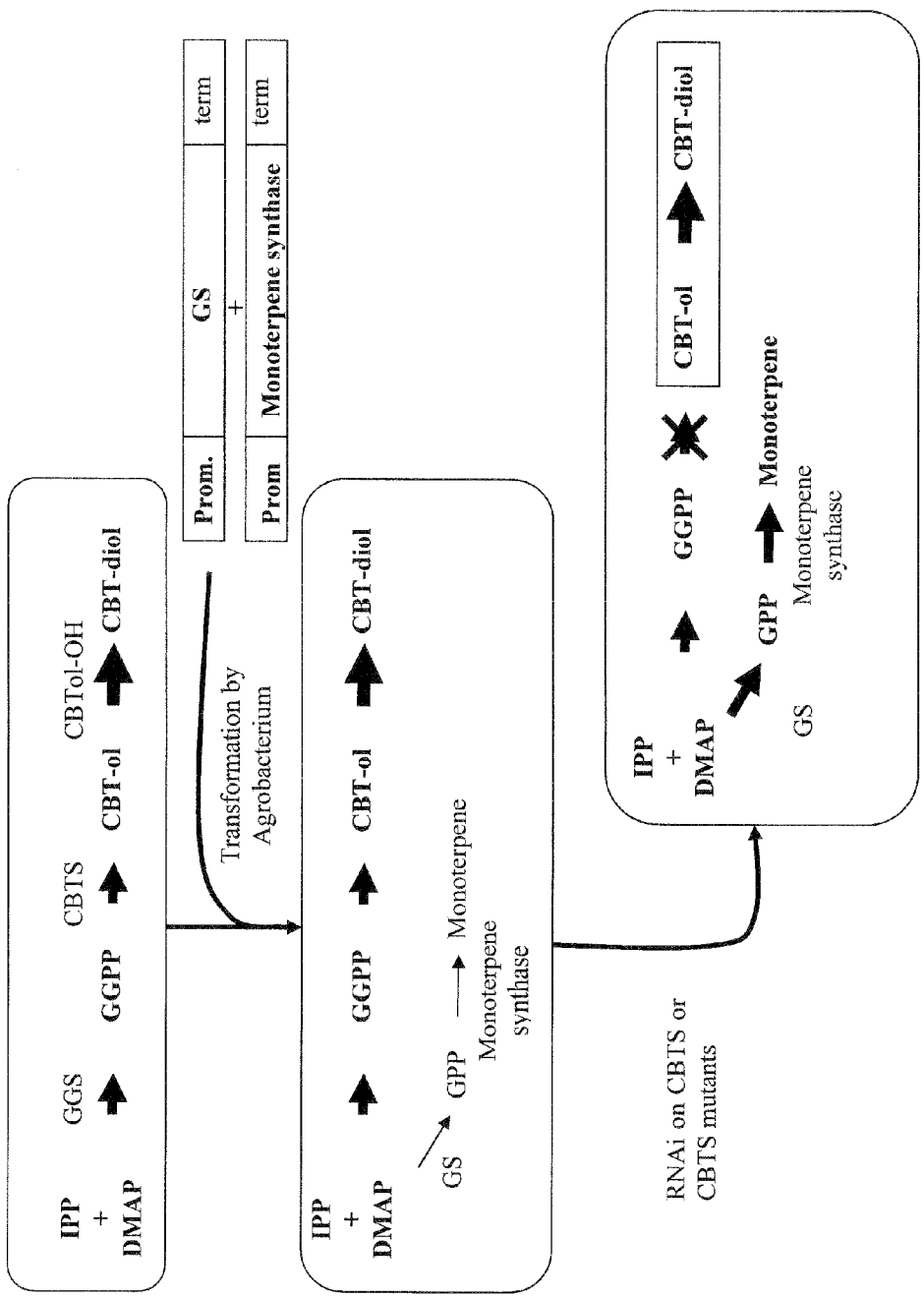
FIG. 9: Outline of the steps leading to monoterpene production in tobacco trichomes (*Nicotiana sylvestris*). Legend: GGS: geranylgeranylpyrophosphate synthase; GS: geranylpyrophosphate synthase and idem FIG. 7.
Figure 10:
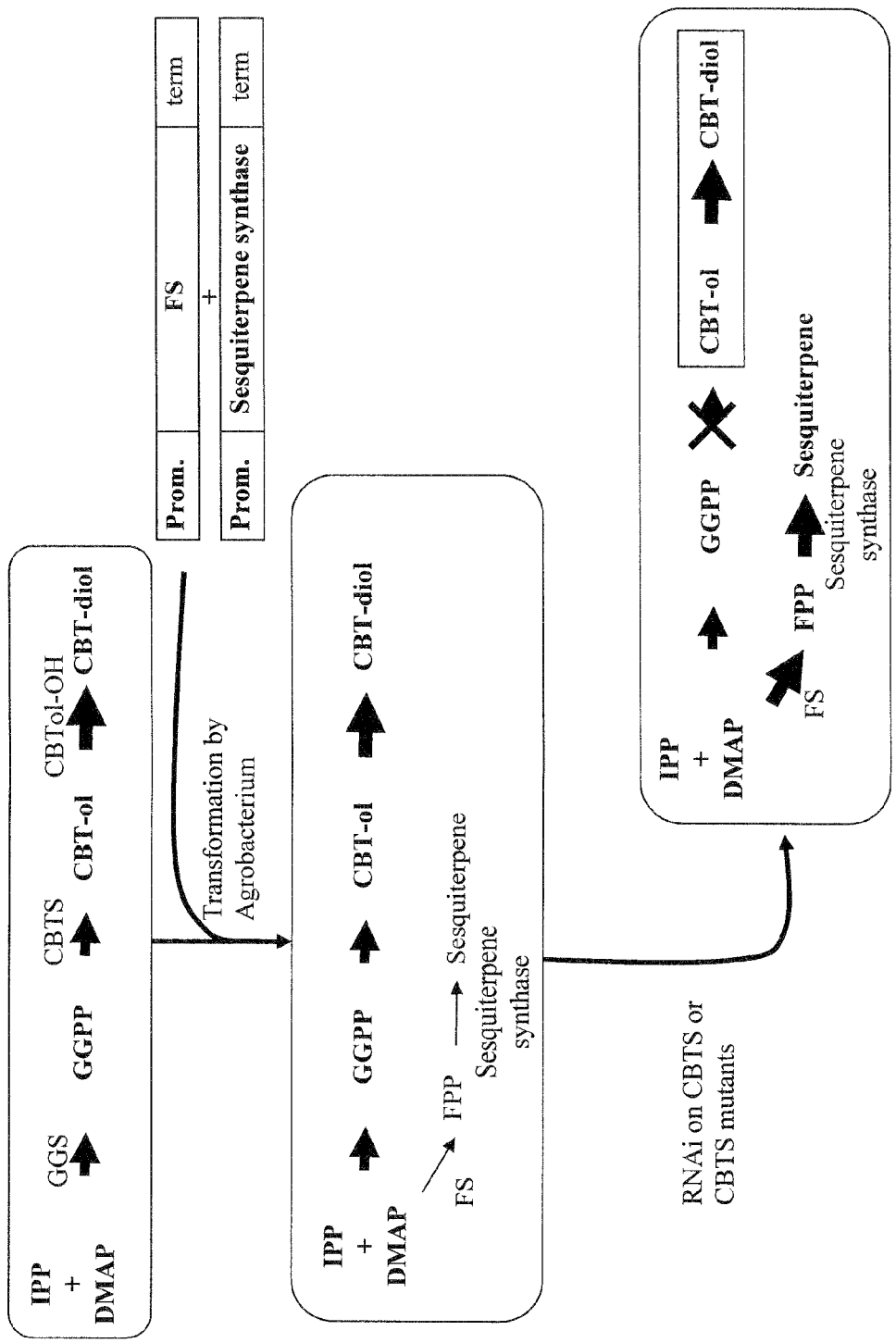
FIG. 10: Outline of the steps leading to sesquiterpene production in tobacco trichomes (*Nicotiana sylvestris*). Legend: FS: farnesylpyrophosphate synthase and idem FIGS. 7 and 8.
Figure 11:
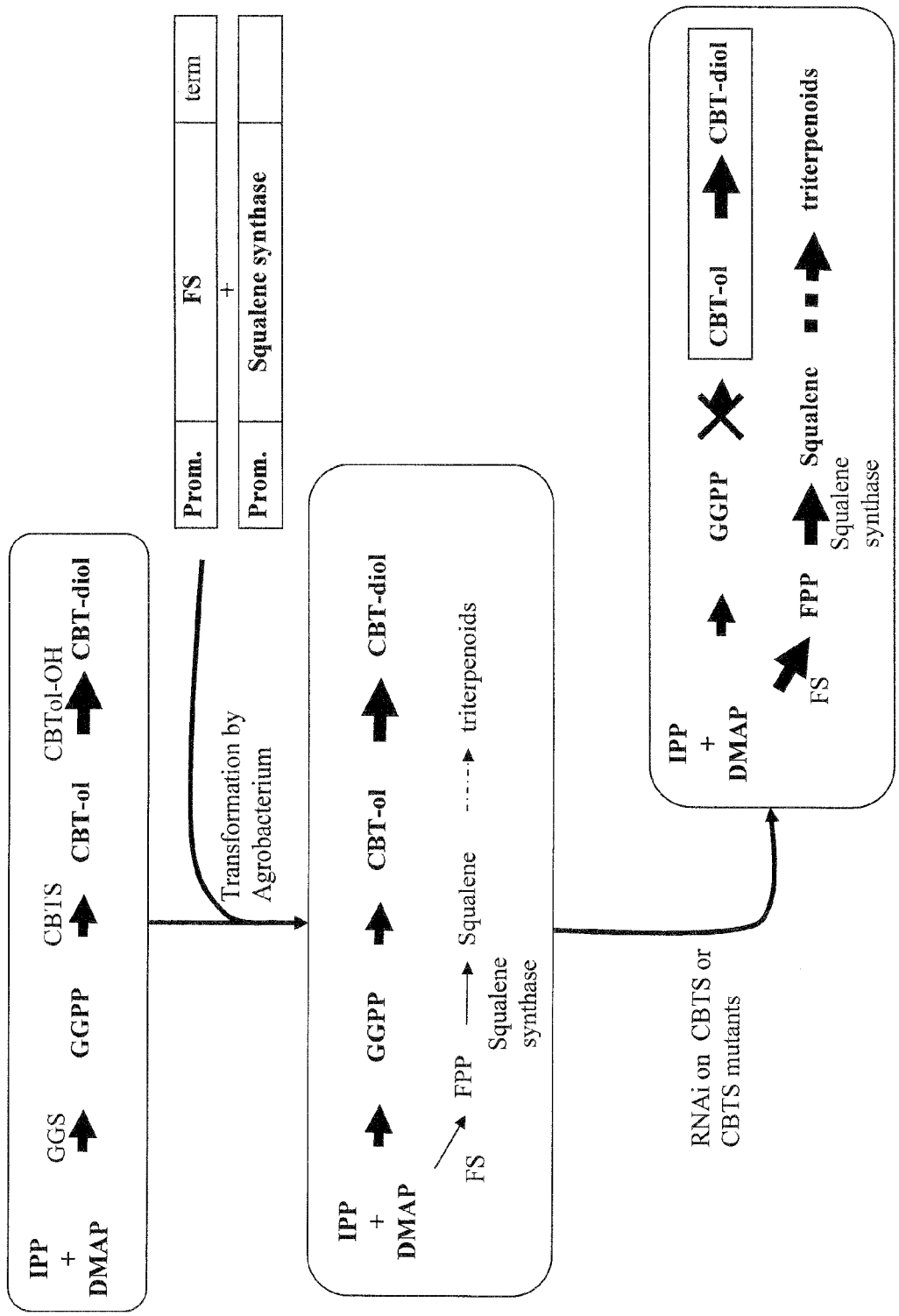
FIG. 11: Outline of the steps leading to triterpene production in tobacco trichomes (*Nicotiana sylvestris*).

The expression of taxadiene synthase under the control of the 1.8 kb promoter of the CYP71D16 gene was compared with expression of the gene encoding taxadiene-5α-hydroxylase under the control of the same promoter but preceded by an enhancer of the 35S promoter (SEQ ID No. 9). Quantitative analysis of expression was carried out by real-time quantitative PCR and by the use of TaqMan® probes specific of the genes. The results in FIG. 7 indicate that expression of the taxadiene-5α-hydroxylase gene was 1000-fold higher than expression of the taxadiene synthase gene. It can be deduced that the 35S promoter enhancer was responsible for this activation since the promoters were identical in all other respects.

Increased Efficiency of Genetic Transformation by *Agrobacterium tumefaciens*.

Figure 12:
FIG. 12: Illustration of the increased efficiency of genetic transformation obtained on leaf discs from the leaves of *N. sylvestris* plants in which CBT-diol production was sharply reduced. The photograph was taken three weeks after co-culture with the same *Agrobacterium tumefaciens* strain containing a kanamycin resistance gene and a transgene of interest. WT: *N. sylvestris*; ihpTPS: *N. sylvestris* containing the ihpTPS transgene.

A homozygote line carrying the ihpTPS transgene (line #804) was generated from *Nicotiana sylvestris*. This line no longer produces CBT-diol at the leaf surface (see FIG. 6). Leaf discs obtained from leaves of *N. sylvestris* and from line #804 were infected with different strains of *Agrobacterium tumefaciens* containing a T-DNA carrying a kanamycin resistance gene and different transgenes of interest (Table 2). After three days of co-culture with *Agrobacterium tumefaciens*, the leaf discs were transferred to selective medium containing kanamycin (150 mg/L). After four weeks of selection, a larger number of resistant calluses appeared on leaf discs from line #804 (FIG. 12). Altogether, the number of transformed plants obtained with line #804 was 5 to 10 times higher than with the *N. sylvestris* control. These findings were confirmed by several experiments using *Agrobacterium* strains carrying different transgenes (Table 2). In conclusion, eliminating CBT-diol secretion at the leaf surface improves the efficiency of genetic transformation.

Identification of the Function of a Gene Encoding a Cytochrome P450 Monooxygenase from Yew.

Figures 13A, 13B:
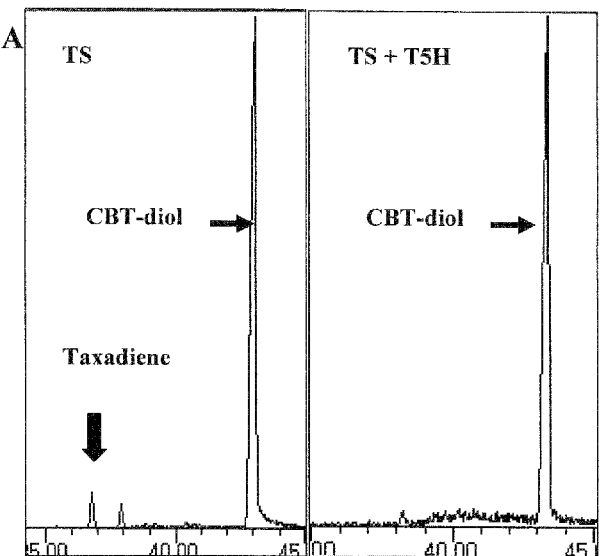
FIG. 13A. TS: Chromatogram of exudate from plants expressing taxadiene synthase alone. Taxadiene was detected in the exudate by GC/MS by extracting the ion 122, characteristic of taxadiene.
FIG. 13B. TS+T5H: GC-MS chromatogram (ion extracted: 191) of exudate from plants expressing taxadiene synthase (TS) and taxadiene 5-hydroxylase (T5H). Taxadiene was no longer visible and no other product was visible other than CBT-diol.
Figures 13C, 13D:
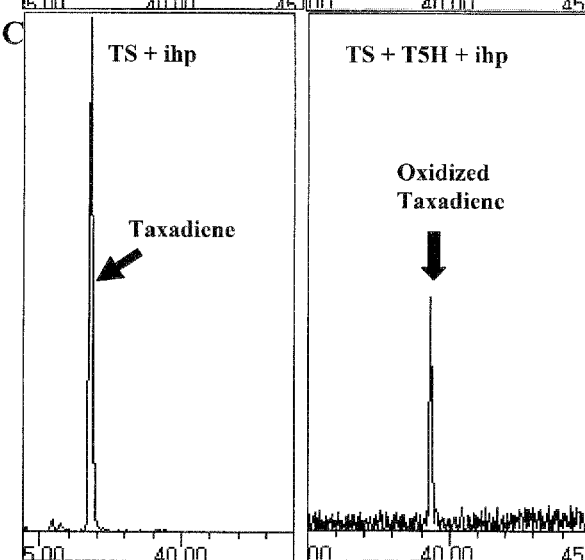
FIG. 13C. TS+ihpTPS. GC-MS chromatogram (ion extracted: 122) of exudate from plants expressing TS in an ihpTPS background. CBT-diol was eliminated, facilitating the detection of taxadiene.
FIG. 13D. TS+T5H+ihpTPS. GC-MS chromatogram (ion extracted: 191) of exudate from plants expressing TS and T5H in an ihpTPS background. CBT-diol was no longer detectable, but a peak corresponding to an oxidized taxadiene (product of the action of taxadiene 5-hydroxylase on taxadiene) was easily detected.

A transgene coding for taxadiene synthase (NID: U48796) under the control of a trichome-specific promoter (patent application No. FR 0410799) and a transgene coding for a taxadiene 5-hydroxylase (T5H, NID: AY289209) under the control of the same promoter were introduced by *Agrobacterium tumefaciens* into *N. sylvestris* and into line ihpTPS (#804). The exudate of the leaves of transformed plants was extracted by soaking the leaves in pentane. The compounds present in the exudate were analysed by gas chromatography followed by mass spectrometric detection (GC-MS). Plants containing only the taxadiene synthase transgene produced taxadiene in the exudate (FIG. 13A). Plants containing both transgenes did not produce taxadiene, confirming that taxadiene is the substrate of T5H. In ihpTPS plants, a new major product became highly visible on the GC-MS chromatogram (FIG. 13D). Due to the abundance of CBT-diol in the exudates of *N. sylvestris* plants, said product was not detectable in these plants which also contained the two transgenes (FIG. 13B). In conclusion, the very low levels of CBT-diol in the exudate of the ihpTPS line made it easier to identify the product of an enzyme expressed in the trichomes and therefore to determine the function of the corresponding genes. Furthermore, the product can also be purified easily, thereby enabling the characterization and production thereof.

REFERENCES

Altschul S F, Gish W, Miller W, Myers E W, Lipman, D J (1990) *J. Mol. Biol.* 215:403-410

Aubourg S, Lecharny A, Bohlmann J (2002) Genomic analysis of the terpenoid synthase (AtTPS) gene family of *Arabidopsis thaliana*. *Mol. Genet. Genomics* 267:730-745.

Bohlmann J, Meyer-Gauen G, Croteau R (1998) Plant terpenoid synthases: molecular biology and phylogenetic analysis. *Proc. Natl. Acad. Sci. USA* 95:4126-33.

Baulcombe D (2004) RNA silencing in plants. *Nature* 431:356-363.

Besumbes O, Sauret-Gueto S, Phillips M A, Imperial S, Rodriguez-Concepcion M, Boronat A (2004) Metabolic engineering of isoprenoid biosynthesis in *Arabidopsis* for the production of taxadiene, the first committed precursor of Taxol. *Biotechnol. Bioeng.* 88:168-75.

Botella-Pavia P, Besumbes O, Phillips M A, Carretero-Paulet L, Boronat A, Rodriguez-Concepcion M (2004) Regulation of carotenoid biosynthesis in plants: evidence for a key role of hydroxymethylbutenyl diphosphate reductase in controlling the supply of plastidial isoprenoid precursors. *Plant J.* 40:188-99.

Broothaerts W, Mitchell H J, Weir B, Kaines S, Smith L M, Yang W, Mayer J E, Roa-Rodriguez C, Jefferson R A (2005). Gene transfer to plants by diverse species of bacteria. *Nature* 433:629-633.

Cho E M, Okada A, Kenmoku H, Otomo K, Toyomasu T, Mitsuhashi W, Sassa T, Yajima A, Yabuta G, Mori K, Oikawa H, Toshima H, Shibuya N, Nojiri H, Omori T, Nishiyama M, Yamane H (2004) Molecular cloning and characterization of a cDNA encoding ent-cassa-12,15-diene synthase, a putative diterpenoid phytoalexin biosynthetic enzyme, from suspension-cultured rice cells treated with a chitin elicitor. *Plant J.* 37:1-8.

Chorianopoulos N, Kalpoutzakis E, Aligiannis N, Mitaku S, Nychas G J, Haroutounian S A (2004). Essential oils of *Satureja*, *Origanum*, and *Thymus* species: chemical composition and antibacterial activities against foodborne pathogens. *J Agric Food Chem.* 52:8261-8267.

Ebinuma H, Sugita K, Matsunaga E, Yamakado M (1997) Selection of marker-free transgenic plants using the isopentenyl transferase gene. *Proc. Natl. Acad. Sci. USA* March 18; 94(6):2117-2121.

Fray R G, Wallace A, Fraser P D, Valero D, Hedden P, Bramley P M, Grierson D (1995) Constitutive expression of a fruit phytoene synthase gene in transgenic tomatoes causes dwarfism by redirecting metabolites from the gibberellin pathway. *Plant J.* 8:693-701.

Friedman M, Henika P R, Levin C E, Mandrell R E (2004). Antibacterial activities of plant essential oils and their components against *Escherichia coli* O157:H7 and *Salmonella enterica* in apple juice. *J Agric Food Chem.* 52:6042-6048.

Hansen G, Wright M S (1999) Recent advances in the transformation of plants. *Trends Plant Sci.* 4: 226-231.

Heemann V, Brümmer U, Paulsen C, Seehofer F (1983) Composition of the leaf surface gum of some *Nicotiana species* and *Nicotiana tabacum* cultivars. *Phytochem.* 22:133-135.

Hooykaas P J, Schilperoort R A (1992) *Agrobacterium* and plant genetic engineering. *Plant Mol. Biol.* 20:175.

Horsch R B, Rogers S G, Fraley R T (1985) Transgenic plants. *Cold Spring Harb Symp. Quant. Biol.* 50:433-7.

Jennewein S, Croteau R (2001) Taxol: biosynthesis, molecular genetics, and biotechnological applications. *Appl. Microbiol. Biotechnol.* 57:13-9.

Jennewein S, Wildung M R, Chau M, Walker K, Croteau R (2004) Random sequencing of an induced *Taxus* cell cDNA library for identification of clones involved in Taxol biosynthesis. *Proc. Natl. Acad. Sci. USA* 101:9149-9154.

Martin D M, Faldt J, Bohlmann J (2004) Functional characterization of nine Norway Spruce TPS genes and evolution of gymnosperm terpene synthases of the TPS-d subfamily. *Plant Physiol.* 135:1908-1927.

Mau C J, West C (1994) Cloning of casbene synthase cDNA: evidence for conserved structural features among terpenoid cyclases in plants. *Proc. Natl. Acad. Sci. USA* 91:8497-8501.

McGarvey P, Kaper J M (1991) A simple and rapid method for screening transgenic plants using the PCR. *Biotechniques* October; 11 (4):428-32.

Peters R J, Flory J E, Jetter R, Ravn M M, Lee H J, Coates R M, Croteau R B (2000) Abietadiene synthase from grand fir (*Abies grandis*): characterization and mechanism of action of the "pseudomature" recombinant enzyme. *Biochemistry* 39:15592-15602.

Prisic S, Xu M, Wilderman P R, Peters R J (2004) Rice Contains Two Disparate ent-Copalyl Diphosphate Synthases with Distinct Metabolic Functions. *Plant Physiol.* 136:4228-4236.

Rios J L, Recio M C (2005). Medicinal plants and antimicrobial activity. *J Ethnopharmacol.* 100:80-84.

Saroglou V, Karioti A, Demetzos C, Dimas K, Skaltsa H (2005) Sesquiterpene lactones from *Centaurea spinosa* and their antibacterial and cytotoxic activities. *J Nat Prod.* 68:1404-1407.

Schepmann H G, Pang J, Matsuda S P (2001) Cloning and characterization of *Ginkgo biloba* levopimaradiene synthase which catalyzes the first committed step in ginkgolide biosynthesis. *Arch. Biochem. Biophys.* 392:263-269.

Seo S, Seto H, Koshino H, Yoshida S, Ohashi Y (2003) A diterpene as an endogenous signal for the activation of defense responses to infection with tobacco mosaic virus and wounding in tobacco. *Plant Cell.* 15:863-873.

Severson R F, Johnson A W, Jackson D M (1985) Cuticular constituents of tobacco: factors affecting their production and their role in insect and disease resistance and smoke quality. *Recent Advances in Tobacco Science* 11:105-173.

Siemens J, and Schieder A (1996) *Plant Tiss. Cult. Biotechnol.* 2:66-75.

Smith N A, Singh S P, Wang M B, Stoutjesdijk P A, Green A G, Waterhouse P M (2000) Total silencing by intron-spliced hairpin RNAs. *Nature* 407:319-20.

Sun T P, Kamiya Y (1994) The *Arabidopsis* GA1 locus encodes the cyclase ent-kaurene synthetase A of gibberellin biosynthesis. *Plant Cell.* 6:1509-1518.

Tissier A, MontanéM-H (1999) Methods for producing a library of mutants and applications thereof. French patent No. 9913515.

Tissier A, Sallaud C, Rontein D (2004) Plant promoters and uses thereof. French patent application No. FR 0410799.

Trapp S C, Croteau R B (2001) Genomic organization of plant terpene synthases and molecular evolutionary implications. *Genetics* 158:811-832.

Trombetta D, Castelli F, Sarpietro M G, Venuti V, Cristani M, Daniele C, Saija A, Mazzanti G, Bisignano G (2005) Mechanisms of antibacterial action of three monoterpenes. *Antimicrob Agents Chemother.* 49:2474-2478

Turner G W, Gershenzon J, Croteau R (2000) Development of peltate glandular trichomes of peppermint. *Plant Phys.* 124:665-680.

Wagner G J, Wang E, Shepherd R W (2004) New approaches for studying and exploiting an old protuberance, the plant trichome. *Annals of Botany* 93:3-11.

Wang E, Wang R, DeParasis J, Loughrin J H, Gan S, Wagner G J (2001) Suppression of a P450 hydroxylase gene in plant trichome glands enhances natural-product-based aphid resistance. *Nat. Biotechnol.* 19:371-374.

Wang E, Wagner G J (2003) Elucidation of the functions of genes central to diterpene metabolism in tobacco trichomes using posttranscriptional gene silencing. *Planta* 216:686-691.

Wang M-B, Graham M W, Waterhouse P M (1999) Methods and means for obtaining modified phenotypes. Patent application WO9953050.

Wesley S V, Helliwell C A, Smith N A, Wang M B, Rouse D T, Liu Q, Gooding P S, Singh S P, Abbott D, Stoutjesdijk P A, Robinson S P, Gleave A P, Green A G, Waterhouse P M (2001) Construct design for efficient, effective and high-throughput gene silencing in plants. *Plant J.* 27:581-90.

Wilderman P R, Xu M, Jin Y, Coates R M, Peters R J (2004) Identification of syn-pimara-7,15-diene synthase reveals functional clustering of terpene synthases involved in rice phytoalexin/allelochemical biosynthesis. *Plant Physiol.* 135:2098-2105.

Wildung M R, Croteau R (1994) A cDNA clone for taxadiene synthase, the diterpene cyclase that catalyses the committed step of taxol biosynthesis. *J. Biol. Chem.* 271:9201-9204.

TABLE 1

| Gene abbreviation | Name of gene | Plants | Promoter (bp) | Transformed plant | Expression | References |
|---|---|---|---|---|---|---|
| LTP3 | Lipid transfer protein | Cotton | 1548 1143 614 | Tobacco | Trichomes, peripheral epidermis of leaves and vascular tissues | Liu et al., 2000, BBA, 1487: 106111 |
| LTP6 | Lipid transfer protein | Cotton | 447 272 | Tobacco | Trichomes and stomata guard cells | Hsu et al., 1999, Plant Science, 143: 6370 |
| wax9D | Lipid transfer protein | *Brassica oleracea* | 972 | Tobacco | Epidermis of leaves, stems and flowers, petals, sepals, ovules, | Pyee and Kolattukudy, 1995, Plant J. 7: 4559 |

TABLE 1-continued

| Gene abbreviation | Name of gene | Plants | Promoter (bp) | Transformed plant | Expression | References |
|---|---|---|---|---|---|---|
| LTP1 | Lipid transfer protein | Arabidopsis | 1149 | Arabidopsis | Epidermal cells of various tissues | Thoma et al., 1994, Plant Physiol. 105 3545 |
| CYC71D16 | CBTol hydroxylase | Tobacco | 1852 | Tobacco | Trichomes | Wang et al., 2002, J. Exp. Bot. 18911897 |

Table 2.

Comparison of transformation efficiency for *N. Sylvestris* versus line #804. Km: Kanamycin; No.: number; #804: *N. sylvestris* carrying the ihpTPS transgene. Legend of transgenes. FPS: gene (Genbank accession No. AF048747) encoding farnesyl pyrophosphate synthase of tomato; TPFPS: FPS with a chloroplast transit peptide. SSTLH: gene (Genbank accession No. AF279455) encoding germacrene synthase of tomato. TPSSTLH: SSTLH with a chloroplast transit peptide. Casbene: gene (Genbank accession No. L32134) encoding casbene synthase of castor oil plant. GUSi: *Escherichia coli* uidA gene with an intron to prevent expression in bacteria.

| Exp N° | Agrobacterium strain | T-DNA resistance | Transgene | No. of leaf discs | No. of plants obtained (*N. sylvestris*) | No. of plants obtained (#804) |
|---|---|---|---|---|---|---|
| 1 | LBA4404 | Km | FPS + SSLTH | 100 | 4 | 41 |
| 2 | LBA4404 | Km | Casbene | 65 | 3 | 27 |
| 3 | LBA4404 | Km | GU Si/TPFPS/ TPSS TLH | 140 | 9 | 40 |

The invention claimed is:

1. A transgenic Solanaceae plant or a seed thereof comprising an expression cassette that comprises a polynucleotide sequence encoding a heterologous terpene synthase operably linked to a trichome-specific promoter, the trichome-specific promoter comprising a sequence selected from the group consisting of SEQ ID NOs: 5, 6, 7 and 8, wherein a terpene of interest is synthesized.

2. The transgenic Solanaceae plant or seed according to claim 1, wherein an endogenous terpene production pathway is blocked by inhibiting the expression of an endogenous diterpene synthase.

3. The transgenic Solanaceae plant or seed according to claim 1, wherein said expression cassette comprises at least one enhancer sequence operably linked to the trichome-specific promoter.

4. The transgenic Solanaceae plant or seed according to claim 1, further comprising a transgene encoding a terpene modification enzyme.

5. A method for producing a terpene of interest in a Solanaceae plant, comprising growing a transgenic Solanaceae plant comprising an expression cassette that comprises a polynucleotide sequence encoding a heterologous terpene synthase operably linked to a trichome-specific promoter, said trichome-specific promoter comprising a sequence selected from the group consisting of SEQ ID NOs: 5, 6, 7 and 8 and recovering the terpene of interest contained in the trichomes of said transgenic Solanaceae plant.

6. The method according to claim 5, wherein said expression cassette comprises at least one enhancer sequence operably linked to the promoter.

7. The method according to claim 5, wherein the recovery of the terpene of interest contained in the trichomes of said transgenic Solanaceae plant is carried out by recovering the terpene of interest contained in the exudate of the trichomes.

8. The method according to claim 5, further comprising blocking an endogenous terpene production pathway by inhibiting the expression of an endogenous diterpene synthase.

9. The method according to claim 5, wherein said heterologous terpene synthase is a diterpene synthase.

10. The method according to claim 9, wherein said diterpene synthase is taxadiene synthase.

11. The method according to claim 5, further comprising introducing into the cell of said transgenic Solanaceae plant a transgene coding for a terpene modification enzyme.

12. A method for recovering heterologous terpenes in the exudate of the trichomes of a Solanaceae plant, comprising a) harvesting the aerial parts of the transgenic Solanaceae plant according to claim 1; b) incubating said aerial parts in an apolar or low polarity solvent; and c) eliminating the solvent.

13. The transgenic Solanaceae plant or seed according to claim 1, wherein the heterologous terpene synthase is a diterpene synthase.

14. The transgenic Solanaceae plant or seed according to claim 13, wherein the diterpene synthase is taxadiene synthase.

15. The transgenic Solanaceae plant or seed according to claim 3, wherein said at least one enhancer sequence comprises SEQ ID NO: 9.

16. The transgenic Solanaceae plant or seed according to claim 1, wherein the trichome-specific promoter comprises SEQ ID NO: 5.

17. The transgenic Solanaceae plant or seed according to claim 1, wherein the trichome-specific promoter comprises SEQ ID NO: 6.

18. The transgenic Solanaceae plant or seed according to claim 1, wherein the trichome-specific promoter comprises SEQ ID NO: 7.

19. The transgenic Solanaceae plant or seed according to claim 1, wherein the trichome-specific promoter comprises SEQ ID NO: 8.

\* \* \* \* \*

UNITED STATES PATENT AND TRADEMARK OFFICE
CERTIFICATE OF CORRECTION

PATENT NO. : 9,115,366 B2
APPLICATION NO. : 11/814943
DATED : August 25, 2015
INVENTOR(S) : Alain Tissier, Christophe Sallaud and Denis Rontein It is certified that error appears in the above-identified patent and that said Letters Patent is hereby corrected as shown below:

In the Specification

Column 15,
Lines 37-38, "Montanë" should read --Montané--.

Column 18,
Line 39, "$^{35}$S and" should read --35S and--.

Signed and Sealed this
Nineteenth Day of April, 2016

Michelle K. Lee
*Director of the United States Patent and Trademark Office*

SEQUENCE LISTING

```
<160> NUMBER OF SEQ ID NOS: 9

<210> SEQ ID NO 1
<211> LENGTH: 4720
<212> TYPE: DNA
<213> ORGANISM: artificial sequence
<220> FEATURE:
<223> OTHER INFORMATION: taxadiene synthase expression cassette

<400> SEQUENCE: 1
gaattccaat cccacaaaaa tctgagctta acagcacagt tgctcctctc agagcagaat      60
cgggtattca acaccctcat atcaactact acgttgtgta taacggtcca catgccggta     120
tatacgatga ctggggttgt acaaaggcag caacaaacgg cgttcccgga gttgcacaca     180
agaaatttgc cactattaca gaggcaagag cagcagctga cgcgtataca acaagtcagc     240
aaacagatag gttgaacttc atccccaaag gagaagctca actcaagccc aagagctttg     300
ctaaggccct aacaagccca ccaaagcaaa aagcccactg gctcacgcta ggaaccaaaa     360
ggcccagcag tgatctagcc ccaaaagaga tctccttgc cccggagatt acaatggacg      420
acttcctcta tctctacgat ctaggaagaa agttcgacgg tgaaggtgac gacaccatgt     480
tcaccactga taatgagaag attagcctct tcaatttcag aaagaatgct gacccacaga     540
tggttagaga ggcctacgca gcaggcctca tcaagacgat ctacccgagt aacaatctcc     600
aggagatcaa ataccttccc aagaaggtta aagatgcagt caaaagattc aggactaact     660
gcatcaagaa cacagagaaa gatatatttc tcaagatcag aagtactatt ccagtatgga     720
cgattcaagg cttgcttcat aaaccaaggc aagtaataga gattggagtc tctaaaaagg     780
tagttcctac tgaatcaaag gccatggagt caaagattca aatagaggac ctaacagaac     840
tcgccgtgaa aactggcgaa cagttcatac agagtctttt acgactcaat gacaagaaga     900
aaatcttcgt caacatggtg gagcacgaca ctcttgtcta ctccaaaaat atcaaagata     960
```

```
cagtctcaga agaccaaagg gctattgaga cttttcaaca aagggtaatt tcgggaaacc    1020
tccttggatt ccattgccca gctatctgtc acttcatcga aaggacagta gaaaaggaag    1080
gtggctccta caaatgccat cattgcgata aaggaaaggc tatcgttcaa gatgcctctg    1140
ccgacagtgg tcccaaagat ggaccccac ccacgaggag catcgtggaa aaagaagacg     1200
ttccaaccac gtcttcaaag caagtggatt gatgtgacat ctccactgac gtaagggatg    1260
acgcacaatc ccactatcct tcgcaagacc cttcctctat ataaggaagt tcatttcatt    1320
tggagaggac acgctcgagt ataagagctc tatttttaca acaattacca acaacaacaa    1380
acaacaaaca acattacaat tacatttaca attaccatgg ctcagctctc atttaatgca    1440
gcgctgaaga tgaacgcatt ggggaacaag gcaatccacg atccaacgaa ttgcagagcc    1500
aaatctgagc gccaaatgat gtgggtttgc tccagatcag gcgaaccag agtaaaaatg     1560 tcgagaggaa gtggtggtcc tggtcctgtc gtaatgatga gcagcagcac tggcactagc    1620
aaggtggttt ccgagacttc cagtaccatt gtggatgata tccctcgact ctccgccaat    1680
tatcatggcg atctgtggca ccacaatgtt atacaaactc tggagacacc gtttcgtgag    1740
agttctactt accaagaacg ggcagatgag ctggttgtga aaattaaaga tatgttcaat    1800
gcgctcggag acgagatat cagtccgtct gcatacgaca ctgcgtgggt ggcgaggctg     1860
gcgaccattt cctctgatgg atctgagaag ccacggtttc ctcaggccct caactgggtt    1920
ttcaacaacc agctccagga tggatcgtgg ggtatcgaat cgcactttag tttatgcgat    1980
cgattgctta acacgaccaa ttctgttatc gccctctcgg tttggaaaac agggcacagc    2040
caagtacaac aaggtgctga gtttattgca gagaatctaa gattactcaa tgaggaagat    2100
gagttgtccc cggatttcca ataatctttt cctgctctgc tgcaaaaggc aaaagcgttg    2160
gggatcaatc ttccttacga tcttccatttt atcaaatatt tgtcgacaac acgggaagcc   2220
aggcttacag atgtttctgc ggcagcagac aatattccag ccaacatgtt gaatgcgttg    2280
gaaggtctcg aggaagttat tgactggaac aagattatga ggtttcaaag taaagatgga    2340
tctttcctga gctcccctgc ctccactgcc tgtgtactga tgaatacagg ggacgaaaaa    2400
tgtttcactt ttctcaacaa tctgctcgac aaattcggcg gctgcgtgcc ctgtatgtat    2460
tccatcgatc tgctggaacg cctttcgctg gttgataaca ttgagcatct cggaatcggt    2520
cgccatttca acaagaaat caaaggagct cttgattatg tctacagaca ttggagtgaa     2580
aggggcatcg gttggggcag agacagcctt gttccagatc tcaacaccac agccctcggc    2640
ctgcgaactc ttcgcatgca cggatacaat gtttcttcag acgttttgaa taatttcaaa    2700
gatgaaaacg ggcggttctt ctcctctgcg ggccaaaccc atgtcgaatt gagaagcgtg    2760
gtgaatcttt tcagagcttc cgaccttgca tttcctgacg aaagagctat ggacgatgct    2820
agaaaatttg cagaaccata tcttagagag gcacttgcaa cgaaaatctc aaccaataca    2880
aaactattca aagagattga gtacgtggtg gagtacccct tggcacatga gtatcccacgc   2940 ttagaagcca gaagttatat tgattcatat gacgacaatt atgtatggca gaggaagact    3000
ctatatagaa tgccatcttt gagtaattca aaatgtttag aattggcaaa attggacttc    3060
aatatcgtac aatctttgca tcaagaggag ttgaagcttc taacaagatg gtggaaggaa    3120
tccggcatgg cagatataaa tttcactcga caccgagtgg cggaggttta ttttttcatca   3180 gctacatttg aacccgaata ttctgccact agaattgcct tcacaaaaat tggttgttta    3240
caagtccttt ttgatgatat ggctgacatc tttgcaacac tagatgaatt gaaaagtttc    3300
actgagggag taaagagatg ggatacatct ttgctacatg agattccaga gtgtatgcaa    3360
```

```
acttgcttta aagtttggtt caaattaatg gaagaagtaa ataatgatgt ggttaaggta      3420
caaggacgtg acatgctcgc tcacataaga aaccctggg agttgtactt caattgttat      3480
gtacaagaaa gggagtggct tgaagccggg tatataccaa cttttgaaga gtacttaaag     3540
acttatgcta tatcagtagg ccttggaccg tgtaccctac aaccaatact actaatgggt    3600
gagcttgtga agatgatgt tgttgagaaa gtgcactatc cctcaaatat gtttgagctt     3660
gtatccttga gctggcgact aacaaacgac accaaaacat atcaggctga aaaggctcga    3720
ggacaacaag cctcaggcat agcatgctat atgaaggata tccaggagc aactgaggaa     3780 gatgccatta agcacatatg tcgtgttgtt gatcgggcct tgaaagaagc aagctttgaa   3840
tatttcaaac catccaatga tatcccaatg ggttgcaagt cctttatttt taaccttaga    3900
ttgtgtgtcc aaatctttta caagtttata gatgggtacg gaatcgccaa tgaggagatt   3960
aaggactata taagaaaagt ttatattgat ccaattcaag tatgaggatc ctctagagtc    4020
ctgctttaat gagatatgcg agacgcctat gatcgcatga tatttgcttt caattctgtt  4080
gtgcacgttg taaaaaacct gagcatgtgt agctcagatc cttaccgccg gtttcggttc   4140
attctaatga atatatcacc cgttactatc gtattttat gaataatatt ctccgttcaa    4200
tttactgatt gtaccctact acttatatgt acaatattaa atgaaaaaca atatattgtg    4260
ctgaataggt ttatagcgac atctatgata gagcgccaca ataacaaaca attgcgtttt   4320
attattacaa atccaatttt aaaaaaagcg gcagaaccgg tcaaacctaa aagactgatt  4380
acataaatct tattcaaatt tcaaaagtgc cccaggggct agtatctacg acacaccgag   4440
cggcgaacta ataacgctca ctgaagggaa ctccggttcc ccgccggcgc gcatgggtga    4500
gattccttga agttgagtat tggccgtccg ctctaccgaa agttacgggc accattcaac    4560
ccggtccagc acggcggccg ggtaaccgac ttgctgcccc gagaattatg cagcatttt    4620 ttggtgtatg tgggccccaa atgaagtgca ggtcaaacct tgacagtgac gacaaatcgt   4680
tgggcgggtc cagggcgaat tttgcgacaa cagtctgcag                          4720
```

<210> SEQ ID NO 2
<211> LENGTH: 4225
<212> TYPE: DNA
<213> ORGANISM: artificial sequence
<220> FEATURE:
<223> OTHER INFORMATION: taxadiene synthase expression cassette
<220> FEATURE:
<221> NAME/KEY: misc_feature
<222> LOCATION: (4028)..(4028)
<223> OTHER INFORMATION: n = a, t, g or c

<400> SEQUENCE: 2

```
gaattcaatt tattttttgta aaacttctct aatttttgga caaactctta tattgatttt     60
ttaatcgaag ccaaaatatt tatttaacta tgaaaaaatt ttaacaacta atttattatg    120
gtaaataata ttgatatggt aacttcaagc acatgacaaa aattataact aactgcagaa    180
gtttattgtc tctctgaatc ttgtggctat atcataacaa atacttgtag ctaataagcc    240
aacgatgttc tcggtttcat ataatttgaa tttaaaata gttttaaat ttaatattta     300 tttcaaatca ttattgtggc taacatgtta taatcgcagt aatatttgga gatgcaatac     360
ttatatttag ctacaaaatt ttattgtatc agaataagtt tgtagctatt aagttagttt    420
ttgccacaaa tttttataat tgaagcaaaa atacttattc agctacagta ttttgtatcg    480
agtaatattt tgtgactaga agattaatat tgctacagta atttcagacg tgtggcaaaa   540
```

```
actcataatt agctacaaaa tattgtcgta gcaataattt tttatatcta ttaatgcaat      600
tattactaca tgcttttata acttgaggca aaaatatcta atagctataa cattttgtta      660
gaagtaattt ttgtggctat aaaattggta ttgctacagt aatttcaaat gcgtggcaaa      720
aaaatacgat taactacgaa attttattgt agcaataact ttgtagctat ttgggtaata      780
ttgctacgac agttagcaat tatagcaaaa atgccaaatc agctttgtca atttaatttt      840
gtagctaatt ttttatgaa attgtaaata gctatgaaat tttaattttt gtggctattg       900
tcaggtatta gccacatata gctaagaatt tgtagctata tatacataat gttgtagtgg      960
caaattctaa cattgtacgc ttggctgccc ttttttttt ttttggctac aaaactctaa      1020
agtaaaggaa ctagaaaact cgtttggcga gagaaagaga gagccatggc tcagctctca     1080
tttaatgcag cgctgaagat gaacgcattg gggaacaagg caatccacga tccaacgaat     1140
tgcagagcca atctgagcg ccaaatgatg tgggtttgct ccagatcagg gcgaaccaga      1200
gtaaaaatgt cgagaggaag tggtggtcct ggtcctgtcg taatgatgag cagcagcact     1260
ggcactagca aggtggtttc cgagacttcc agtaccattg tggatgatat ccctcgactc     1320
tccgccaatt atcatggcga tctgtggcac cacaatgtta tacaaactct ggagacaccg     1380
tttcgtgaga gttctactta ccaagaacgg gcagatgagc tggttgtgaa aattaaagat     1440
atgttcaatg cgctcggaga cggagatatc agtccgtctg catacgacac tgcgtgggtg     1500
gcgaggctgg cgaccatttc ctctgatgga tctgagaagc cacggtttcc tcaggccctc     1560
aactgggttt caacaacca gctccaggat ggatcgtggg gtatcgaatc gcactttagt      1620
ttatgcgatc gattgcttaa cacgaccaat tctgttatcg ccctctcggt ttggaaaaca     1680
gggcacagcc aagtacaaca aggtgctgag tttattgcag agaatctaag attactcaat     1740
gaggaagatg agttgtcccc ggatttccaa ataatctttc ctgctctgct gcaaaaggca     1800
aaagcgttgg ggatcaatct tccttacgat cttccattta tcaaatattt gtcgacaaca     1860
cgggaagcca ggcttacaga tgtttctgcg gcagcagaca atattccagc caacatgttg     1920
aatgcgttgg aaggtctcga ggaagttatt gactggaaca agattatgag gtttcaaagt     1980
aaagatggat ctttcctgag ctcccctgcc tccactgcct gtgtactgat gaatacaggg     2040
gacgaaaaat gtttcacttt tctcaacaat ctgctcgaca aattcggcgg ctgcgtgccc     2100
tgtatgtatt ccatcgatct gctggaacgc ctttcgctgg ttgataacat tgagcatctc     2160
ggaatcggtc gccatttcaa acaagaaatc aaaggagctc ttgattatgt ctacagacat     2220
tggagtgaaa ggggcatcgg ttggggcaga gacagccttg ttccagatct caacaccaca     2280
gccctcggcc tgcgaactct tcgcatgcac ggatacaatg tttcttcaga cgttttgaat     2340
aatttcaaag atgaaaacgg gcggttcttc tcctctgcgg gccaaaccca tgtcgaattg     2400
agaagcgtgg tgaatctttt cagagcttcc gaccttgcat ttcctgacga aagagctatg     2460
gacgatgcta gaaatttgc agaaccatat cttagagagg cacttgcaac gaaaatctca     2520
accaatacaa aactattcaa agagattgag tacgtggtgg agtacccttg cacatgagt      2580 atcccacgct agaagccag aagttatatt gattcatatg acgacaatta tgtatggcag     2640
aggaagactc tatatagaat gccatctttg agtaattcaa aatgtttaga attggcaaaa     2700
ttggacttca atatcgtaca atctttgcat caagaggagt tgaagcttct aacaagatgg     2760
tggaaggaat ccggcatggc agatataaat ttcactcgac accgagtggc ggaggtttat     2820
ttttcatcag ctacatttga acccgaatat tctgccacta gaattgcctt cacaaaaatt     2880
ggttgtttac aagtcctttt tgatgatatg gctgacatct ttgcaacact agatgaattg     2940
```

```
aaaagtttca ctgagggagt aaagagatgg gatacatctt tgctacatga gattccagag    3000
tgtatgcaaa cttgctttaa agtttggttc aaattaatgg aagaagtaaa taatgatgtg    3060
gttaaggtac aaggacgtga catgctcgct cacataagaa aaccctggga gttgtacttc    3120
aattgttatg tacaagaaag gggagtggctt gaagccgggt atataccaac ttttgaagag    3180
tacttaaaga cttatgctat atcagtaggc cttggaccgt gtaccctaca accaatacta    3240
ctaatgggtg agcttgtgaa agatgatgtt gttgagaaag tgcactatcc ctcaaatatg    3300
tttgagcttg tatccttgag ctggcgacta acaaacgaca ccaaaacata tcaggctgaa    3360
aaggctcgag gacaacaagc ctcaggcata gcatgctata tgaaggataa tccaggagca    3420
actgaggaag atgccattaa gcacatatgt cgtgttgttg atcgggcctt gaaagaagca    3480
agctttgaat atttcaaacc atccaatgat atcccaatgg gttgcaagtc ctttatttttt    3540 aaccttagat tgtgtgtcca aatctttttac aagtttatag atgggtacgg aatcgccaat    3600
gaggagatta aggactatat aagaaaagtt tatattgatc caattcaagt atgaggtacc    3660
ttatatataa caatgcagac acaccttcaa agctgagtat ttggagcaaa tatggaagca    3720
ttttgtattg tccatgtaac ctataagtca cgtgtttggg caatggcaac atttactaat    3780
atttgcatta tggtaggttg tttacatcac acctatcggg ggcgaccctt cctaaacctg    3840
acatgaatgt gtgatgctty gtgcacctgg cggctcattt ttactatttc actgttacaa    3900
cttatttgga cggttgttac ctattgaatc atgtagtatt gttacttgaa tacaatgttt    3960 atttttaatta ttacttaaat tttattctat catatcgtta aatccatcat tacgtaacaa    4020
tgaaaagngt cactttatgg aatgacggat ttagtgtggt ggtgtcattt ccttgcattt    4080
ttctctcatc ttgaccttcc ttattattag ataatcatct tttatcattt atcctacttt    4140
ttatacaata attctactcc atatcctatt tttttcttagt aatgttgcaa gtttattctt    4200
catattgtta gtgcgtattg gatcc                                          4225

<210> SEQ ID NO 3
<211> LENGTH: 3440
<212> TYPE: DNA
<213> ORGANISM: artificial sequence
<220> FEATURE:
<223> OTHER INFORMATION: RNAi construct for NsTPS gene silencing

<400> SEQUENCE: 3
gagctcaaag aggtgaaacc taatctagta tgcaaaccat gttaaattct caattgtttt     60
gatagataat gagttttctg ataattaata aattattaga taattaaagg accaaattta    120
tatgactttt gttttttatc atcttgatca tatatacaat gtaatggata caagcttata    180
gttgtataaa ttctatataa ttagttattc atacattaat tagatatatt caattgttct    240
ttataaatat aattcaaacc tgaaagcaat acttattttg taagaattgc atatattgtta    300 ttttgttatg gacttaaata ttaaccatgt tataatctta agtttatatt attagaaaaa    360
cttagttttt gaaagactaa tatgaacatt agtacttatt tcaaaaataa gcgcttagat    420
atatgaaatt actttaagta cttatttaaa ataattaagt accacacata catacatatc    480
tctacaaact gttaaagttt tctatatgag tacttatttt aaaataagag cataaatata    540
ataaattatg ttaaattctt atttaaaata ataaggacc aaacatgcat aaaataaagt    600
atgagcttaa taagtcaaga agctaattga taagcattga tgccaaatgc acttactaac    660
tgttctatat tgtaggaaaa atctaacttt tatattaaaa atttatttttc ataaaacttc    720
```

```
cctaatttttt gaacaaaatc ttatattgat ttttaatca aagccaaaat atttatttaa      780
ctatgaaaat tttttaacaa ctaatttatt atggtaaata atattgatat ggtaactttc      840
agcacatgac aaaaattata actaactgca gaagtttact gtctctctga atcttgtggc      900
tatgtcattc tatcataaca aatacttgta gctaatacgc caacgatgtt ctcgatttca      960
tataatttga attttaaaat agcttttaaa tttaatattt atttcaaatc attattgtga     1020
ctaacatgtt ataaccgcag taatatttgg agatgcaata cttatattta gctacaaaat     1080
tttattgtat cataataagt ttgtagctat taagttagtt tttgccacaa atttttataa     1140
ttgaagcaaa aatacctatt caactacaat attttgtatc gagtaatatt ttgtgactag     1200
aagattaata ttattacagt aatttctgac gtgtggcaaa aactcataat tatctacaaa     1260
atattgtcgt agcaataatt ttttatatct attaatccaa ttattgctac atgcttttat     1320
aacttgaggc aaaaatatct atttagctat aacattttgt tagaagtaat ttttgtgact     1380
ataaagttgt tattgctaca gtaatttcaa atgcgtggca aaaaaaatac gattagctac     1440
gaaattttat tgtagcaata aatttgtagc tatttgggta atattgctac gacagttagc     1500
aattatagca aaaatgctaa atcagctttg tcgatttaat tttgtagcta atttttttat     1560
gaatttgtaa atagctatga aattttaatt tttgtggcta ttgttaggta ttagccacat     1620
atagctaaga atttgtagct atatatacat aatgttgtag tggcaaattc taacattgta     1680
agcttggctg ccttttttt ttttgggct acaaaactct aaagtaaagg aactagaaaa       1740
ctcgtttggc gagagaaaga gggatccctg caggaaatta ctacccaaga gaaaatgaa      1800 catgaaatgc taaagaaat agttcggaaa atgttggtag aaactccaga taatagtaca      1860
caaaaactag tcttgattga cacaattcaa agattgggat tagcatatca tttcaatgat     1920
gagattgaaa actccattca aaacatcttt aatttgtctc aaaatagtga agatgacgat     1980
gaacacaacc tttatgttgc tgctcttcgt tttcgacttg cgaggcaaca aggatattac     2040
atgtcttcag gtaccttaca tttctgccct ttcccgcaca gcttcatttt ttttcgttgt     2100
taaaagacag ttcggcgcat aaaatatctc atgtatacgc agggtcagga cgaaccgccc     2160 ccaagggggtg taaagtatgc aacttacccct aatactaaat atctcgtgta tacacagggt   2220
caggacaagt cgcacccaag gggtgtaatg tagacaactt atcctaatgc tattagtaac     2280
tgattttatg gctcgaacac ataaattata ggtcacacag taacaacttt accgttgctc     2340
aaagactcgc cttcctcttt ttttagttat cgcaccttat ttgtgcagag aatagcaagt     2400
ttcgagatct gcttctatat agaagacttc tgtattatac ttttttatttt tgtccttctg    2460 cttaaaaata gtaaaaaact atagtgtgga aattgtaaat ttcttaacta gctgtgaaat     2520
caaatagtta ttataggaat attatttaag actccactta tggaaaacca ctgggttgtt    2580
gttgttattg tcaataataa cttggggtac gatttacttc ttttccatg gcttgtccac     2640 gactatattc ctattaacaa tgttgtgact atgctttctt tgagtcgagg gtctattgat    2700
aacaggctct cgatctttac aaggtaaaag taatgtctgc gtacacactc tactccgcag   2760
actccacttg taggatttca ctgaatattt tttgttgttg ttgttgttgt aataacttag    2820
ggtttaattt cttgatgcta atgaaattca tttctttcaa aatataaaca tggtgttcaa    2880
ccagatgtgt tcaagcaatt cactaaccat gagtacttac ctgaagacat gtaatatcct    2940
tgttgcctcg caagtcgaaa acgaagagca gcaacataaa ggttgtgttc atcgtcatct    3000
tcactatttt gagacaaatt aaagatgttt tgaatggagt tttcaatctc atcattgaaa    3060
tgatatgcta atcccaatct ttgaattgtg tcaatcaaga ctagttttg tgtactatta     3120
```

```
tctggagttt ctaccaacat tttccgaact atttcttta gcatttcatg ttcatttttc    3180
tcttgggtag taatttcctc gaggtttctt aagattgaat cctgttgccg gtcttgcgat    3240
gattatcata taatttctgt tgaattacgt taagcatgta ataattaaca tgtaatgcat    3300
gacgttattt atgagatggg ttttatgat tagagtcccg caattataca tttaatacgc    3360
gatagaaaac aaaatatagc gcgcaaacta ggataaatta tcgcgcgcgg tgtcatctat    3420
gttactagat cgggtctaga                                                3440

<210> SEQ ID NO 4
<211> LENGTH: 3442
<212> TYPE: DNA
<213> ORGANISM: artificial sequence
<220> FEATURE:
<223> OTHER INFORMATION: Casbene synthase expression cassette in tobacco
      trichomes
<220> FEATURE:
<221> NAME/KEY: misc_feature
<222> LOCATION: (3245)..(3245)
<223> OTHER INFORMATION: n = a, t, g or c

<400> SEQUENCE: 4
gagctcaatt tattttgta aaacttctct aattttgga caaactctta tattgatttt      60
ttaatcgaag ccaaaatatt tatttaacta tgaaaaaatt ttaacaacta atttattatg    120
gtaaataata ttgatatggt aacttcaagc acatgacaaa aattataact aactgcagaa    180
gtttattgtc tctctgaatc ttgtggctat atcataacaa atacttgtag ctaataagcc    240
aacgatgttc tcggtttcat ataatttgaa tttaaaata gttttaaat ttaatattta    300 tttcaaatca ttattgtggc taacatgtta taatcgcagt aatatttgga gatgcaatac    360
ttatatttag ctacaaaatt ttattgtatc agaataagtt tgtagctatt aagttagttt    420
ttgccacaaa tttttataat tgaagcaaaa atacttattc agctacagta ttttgtatcg    480
agtaatattt tgtgactaga agattaatat tgctacagta atttcagacg tgtggcaaaa    540
actcataatt agctacaaaa tattgtcgta gcaataattt tttatatcta ttaatgcaat    600
tattactaca tgcttttata acttgaggca aaaatatcta atagctataa cattttgtta    660
gaagtaattt ttgtggctat aaaattggta ttgctacagt aatttcaaat gcgtggcaaa    720
aaaatacgat taactacgaa attttattgt agcaataact ttgtagctat ttgggtaata    780
ttgctacgac agttagcaat tatagcaaaa atgccaaatc agctttgtca atttaatttt    840
gtagctaatt ttttatgaa attgtaaata gctatgaaat tttaatttt gtggctattg    900 tcaggtatta gccacatata gctaagaatt tgtagctata tatacataat gttgtagtgg    960
caaattctaa cattgtacgc ttggctgccc ttttttttt ttttggctac aaaactctaa    1020
agtaaaggaa ctagaaaact cgtttggcga gagaaagaga gagccatggc attgccatca    1080
gctgctatgc aatccaaccc tgaaaagctt aacttatttc acagattgtc aagcttaccc    1140
accactagct tggaatatgg caataatcgc ttcccttct tttcctcatc tgccaagtca    1200
cactttaaaa aaccaactca agcatgttta tcctcaacaa cccaccaaga agttcgtcca    1260
ttagcatact ttcctcctac tgtctggggc aatcgctttg cttccttgac cttcaatcca    1320
tcggaatttg aatcgtatga tgaacgggta attgtgctga agaaaaaagt taaggacata    1380
ttaatttcat ctacaagtga ttcagtggag accgttattt taatcgactt attatgtcgg    1440
cttggcgtat catatcactt tgaaaatgat attgaagagc tactaagtaa aatcttcaac    1500
tcccagcctg accttgtcga tgaaaaagaa tgtgatctct acactgcggc aattgtattc    1560
```

```
cgagttttca gacagcatgg ttttaaaatg tcttcggatg tgtttagcaa attcaaggac    1620
agtgatggta agttcaagga atccctacgg ggtgatgcta agggtatgct cagccttttt    1680
gaagcttccc atctaagtgt gcatggagaa gacattcttg aagaagcctt tgctttcacc    1740
aaggattact tacagtcctc tgcagttgag ttattcccta atctcaaaag gcatataacg    1800
aacgccctag agcagccttt ccacagtggc gtgccgaggc tagaggccag gaaattcatc    1860
gatctatacg aagctgatat tgaatgccgg aatgaaactc tgctcgagtt tgcaaagttg    1920
gattataata gagttcagtt attgcaccaa caagagctgt gccagttctc aaagtggtgg    1980
aaagacctga atcttgcttc ggatattcct tatgcaagag acagaatggc agagattttc    2040
ttttgggcag tcgcgatgta ctttgagcct gactatgcac acacccgaat gattattgcg    2100
aaggttgtat tgcttatatc actaatagat gatacaattg atgcgtatgc aacaatggag    2160
gaaactcata ttcttgctga agcagtcgca aggtgggaca tgagctgcct cgagaagctg    2220
ccagattaca tgaaagttat ttataaacta ttgctaaaca ccttctctga attcgagaaa    2280
gaattgacgg cggaaggcaa gtcctacagc gtcaaatacg aagggaagc gtttcaagaa     2340 ctagtgagag gttactacct ggaggctgta tggcgcgacg agggtaaaat accatcgttc    2400
gatgactact tgtataatgg atccatgacc accggattgc ctctcgtctc aacagcttct    2460
ttcatgggag ttcaagaaat tacaggtctc aacgaattcc aatggctgga aactaatccc    2520
aaattaagtt atgcttccgg tgcattcatc cgacttgtca acgacttaac ttctcatgtg    2580
actgaacaac aaagaggaca cgttgcatct tgcatcgact gctatatgaa ccaacatgga    2640
gtttccaaag acgaagcagt caaaatactt caaaaaatgg ctacagattg ttggaaagaa    2700
attaatgaag aatgtatgag gcagagtcaa gtgtcagtgg gtcacctaat gagaatagtt    2760
aatctggcac gtcttacgga tgtgagttac aagtatggag acggttacac tgattcccag    2820
caattgaaac aatttgttaa gggattgttc gttgatccaa tttctatttg aggtacctta    2880
tatataacaa tgcagacaca ccttcaaagc tgagtatttg gagcaaatat ggaagcattt    2940
tgtattgtcc atgtaaccta taagtcacgt gtttgggcaa tggcaacatt tactaatatt    3000
tgcattatgg taggttgttt acatcacacc tatcgggggc gacccttcct aaacctgaca    3060
tgaatgtgtg atgcttygtg cacctggcgg ctcattttta ctatttcact gttacaactt    3120
atttggacgg ttgttaccta ttgaatcatg tagtattgtt acttgaatac aatgtttatt    3180
ttaattatta cttaaatttt attctatcat atcgttaaat ccatcattac gtaacaatga    3240
aaagngtcac tttatggaat gacggattta gtgtggtggt gtcatttcct tgcattttc    3300 tctcatcttg accttcctta ttattagata atcatctttt atcatttatc ctactttta    3360 tacaataatt ctactccata tcctattttt tcttagtaat gttgcaagtt tattcttcat    3420
attgttagtg cgtattgtcg ac                                             3442
```

<210> SEQ ID NO 5
<211> LENGTH: 1068
<212> TYPE: DNA
<213> ORGANISM: Nicotiana sylvestris

<400> SEQUENCE: 5

```
aattttatttt cataaaactt ctctaatttt tgaacaaaat cttatattga ttttttaatc     60
aaagccaaaa tatttattta actatgaaaa ttttttaaca actaatttat tatggtaaat    120
aatattgata tggtaacttc aagcacatga caaaaattat aactaactgc agaagtttac    180
```

```
tgtctctctg aatcttgtgg ctatgtcatt ctatcataac aaatacttgt agctaatacg      240
ccaacgatgt tctcgatttc atataatttg aattttaaaa tagcttttaa atttaatatt      300
tatttcaaat cattattgtg actaacatgt tataaccgca gtaatatttg gagatgcaat      360
acttatattt agctacaaaa ttttattgta tcataataag tttgtagcta ttaagttagt      420
ttttgccaca aattttttata attgaagcaa aaataccctat tcaactacaa tattttgtat    480
cgagtaatat tttgtgacta gaagattaat attattacag taatttcaga cgtgtggcaa      540
aaactcataa ttatctacaa aatattgtcg tagcaataat ttttatatc tattaatcca       600 attattgcta catgctttta aacttgagg caaaaatatc tatttagcta taacattttg       660
ttagaagtaa ttttttgtgac tataaagttg ttattgctac agtaatttca aatgcgtggc     720
aaaaaaaata cgattagcta cgaaaatttta ttgtagcaat aaatttgtag ctatttgggt    780
aatattgcta cgacagttag caattatagc aaaaatgcta aatcagcttt gtcgatttaa     840
ttttgtagct aattttttta tgaatttgta aatagctatg aaattttaat ttttgtggct     900
attgttaggt attagccaca tatagctaag aatttgtagc tatatataca taatgttgta    960
gtggcaaatt ctaacattgt aagcttggct gccttttttt tttttggct acaaaactct     1020 aaagtaaagg aactagaaaa ctcgtttggc gagagaaaga gagagatg                 1068

<210> SEQ ID NO 6
<211> LENGTH: 1060
<212> TYPE: DNA
<213> ORGANISM: Nicotiana sylvestris

<400> SEQUENCE: 6
aatttatttt tgtaaaactt ctctaatttt tggacaaact cttatattga ttttttaatc      60
aaagccaaaa tatttatttta actatgaaaa aattttaaca actaatttat tatggtaaat    120
aatattgata tggtaacttc aagcacatga caaaaattat aactaactgc agaagtttat     180
tgtctctctg aatcttgtgg ctatatcata acaaatactt gtagctaata agccaacgat     240
gttctcggtt tcatataatt tgaattttaa aatagttttt aaatttaata tttatttcaa    300
atcattattg tggctaacat gttataatcg cagtaatatt tggagatgca atacttatat    360
ttagctacaa aattttattg tatcagaata gtttgtagc tattaagtta gttttttgcca     420 caaatttttta taattgaagc aaaaatactt attcagctac agtatttttgt atcgagtaat    480 attttgtgac tagaagatta atattgctac agtaatttca gacgtgtggc aaaaactcat     540
aattagctac aaaatattgt cgtagcaata atttttttata tctattaatg caattattac    600
tacatgcttt tataacttga ggcaaaaata tctaatagct ataacatttt gttagaagta    660 attttgtgg ctataaaaatt ggtattgcta cagtaatttc aaatgcgtgg caaaaaaata    720
cgattaacta cgaaattttta ttgtagcaat aactttgtag ctatttgggt aatattgcta    780
cgacagttag caattatagc aaaaatgcta aatcagcttt gtcaatttaa ttttgtagct     840
aattttttta tgaatttgta aatagctatg aaattttaat ttttgtggct attgttaggt    900
attagccaca tatagctaag aatttgtagc tatatataca taatgttgta gtggcaaatt    960
ctaacattgt acgcttggct gccctttttt tttttttgg ctacaaaact ctaaagtaaa     1020
ggaactagaa aactcgtttg gcgagagaaa gagagagatg                          1060

<210> SEQ ID NO 7
<211> LENGTH: 1060
<212> TYPE: DNA
<213> ORGANISM: Nicotiana sylvestris
```

<400> SEQUENCE: 7

```
aatttatttt cgtaaaattt ctctaatttg dacaaactct tatattgatt tttttaatca    60
aagccaaaat atttatttaa ctatgaaaat tttttaacaa ctaatttatt atggtaaata   120
atattgatat ggtaacttca agcacatgat aaaaattata actaactgca gaagtttact   180
gtctctttga atcttgtggt tatatcattc tatcataaca aatacttgta gctaataagc   240
caacgatgtt ctcggtttca tataatttga atttaaaat agttttaaa tttaatattt   300
atttcaaatt attattgtgg ctaacatgtt ataaccgcag taatatttgg agatgcaata   360
cttatattta gcttgaaaat tttattgtat cagaacaagt tgtagctat taagttagtt   420
tttgccacaa atttttataa ttgaagcaaa atacctatt cagctacagt attttgtatc   480
gagtaatatt ttgtgactag aagattaata ttgctacagt aatttcagac gtgtggcaaa   540
aactcataat tagctacaaa atattgtcgt agcaataatt ttttatatct attaatccaa   600
ttattgctac atgcttttat aacttgaggc aaaaatatct atttagctat aacattttat   660
taaaagtaat ttttgtggct ataaagttgt tattgctaca gtaatttcaa atgcgtggca   720
aaaaaaatac gattagctac gaaattttat tgtagcaata aatttgtagc tatttgggta   780
atattgctac gacagttagc aattatagca aaaatgctaa attagctttg ttaatttaat   840
tttgtagcta aacttttta tgaaatttta atttttgtgg ctattgatag gtattagcta   900
caatttcat atatgtagct aagaatttgt agctatatat acataatgtt gtagtggcaa   960
attctaaacat tgtacgcttg gctgcccttt tttttggct acaaaactct aaagtaaagg  1020
aactagaaaa ctcgtttggc gagagaaaga gagagagatg                         1060
```

<210> SEQ ID NO 8
<211> LENGTH: 1087
<212> TYPE: DNA
<213> ORGANISM: Nicotiana sylvestris

<400> SEQUENCE: 8

```
aatttatttt cgtaaaattt ctctaatttt tggacaaact cttatattgg tttttaatc    60
aaagccaaaa tatttattta actatgaaat tttgttgaac aactaattta ttatggtaaa   120
taatattgat atggtaactt caagcacatg acaaaaatta taactaactg cagaagttta   180
ctgtctctct gaatcttgtg ctatatcat tctatataac aaatacttgt agctaataag   240
ccaacgatgt tctcggtttc atataatttg aattttaaaa tagttttta atttaatatt   300
tatttcaaat cattattgtg gctagcatgt tataaccgca gtaatatttg gagatgcaat   360
acttatattt agctacaaaa ttttattgta tcagaataag tttgtaacta ttaagttagt   420
ttttgccaca aattttata attgaagcaa aatacctat tcagctacga tattttgtat   480
cgagtaatat tttgtgacta gaagattaat attgctagag taatttcaga cgtgtggcaa   540
aaactcataa ttagctacaa atattgtcg tagcaataat tgtttatatc tattaatcca   600
attattgcta tatgctttta aacttgaggg caaaaatatt tatttagcta taacattttg   660
ttagaagtaa ttttttgtggc tataaagttg ttattgctac ggtaatttca aatgcgtggc   720
aaacaaatac gattagctac gaaattttat tgtagcaata aatttgtagc tatttgggta   780
atattgctac gacagttagc aattatagca aaaatgctaa attagctttg tcaatttaat   840
tttttagcta aattttttta taaaattgta aatagccatg aaatttttaat ttttgtggct   900
attgttaggt attagcccaca attttcatat atgtatctaa gaatttgtag ctatatatac   960
```

-continued

```
ataatgttgt agtggcaaat tctaacattg taagcttagc tgcccttttt tttttttttt    1020
tttggctaca aaactctaaa gtaaaggaac tagaaaactc gtttggcgag agaaagaggg    1080
atccatg                                                              1087

<210> SEQ ID NO 9
<211> LENGTH: 630
<212> TYPE: DNA
<213> ORGANISM: artificial sequence
<220> FEATURE:
<223> OTHER INFORMATION: an enhancer of the 35S promoter

<400> SEQUENCE: 9
tacagtctca gaagaccaaa gggctattga gacttttcaa caaagggtaa tatcgggaaa      60
cctcctcgga ttccattgcc cagctatctg tcacttcatc aaaaggacag tagaaaagga    120
aggtggcacc tacaaatgcc atcattgcga taaaggaaag gctatcgttc aagatgcctc    180
tgccgacagt ggtcccaaag atggaccccc acccacgagg agcatcgtgg aaaaagaaga    240
cgttccaacc acgtcttcaa agcaagtgga ttgatgtgaa catggtggag cacgacactc    300
tcgtctactc caagaatatc aaagatacag tctcagaaga ccaaagggct attgagactt    360
ttcaacaaag ggtaatatcg ggaaacctcc tcggattcca ttgcccagct atctgtcact    420
tcatcaaaag gacagtagaa aaggaaggtg gcacctacaa atgccatcat tgcgataaag    480
gaaaggctat cgttcaagat gcctctgccg acagtggtcc caaagatgga cccccaccca    540
cgaggagcat cgtggaaaaa gaagacgttc caaccacgtc ttcaaagcaa gtggattgat    600
gtgatatctc cactgacgta agggatgacg                                      630
```